(12) United States Patent
Mullaney

(10) Patent No.: US 8,419,732 B2
(45) Date of Patent: Apr. 16, 2013

(54) METHOD FOR USING A FIXATOR DEVICE

(75) Inventor: Michael W. Mullaney, Kinnelon, NJ (US)

(73) Assignee: Sixfix, Inc., Memphis, TN (US)

( * ) Notice: Subject to any disclaimer, the term of this patent is extended or adjusted under 35 U.S.C. 154(b) by 2655 days.

(21) Appl. No.: 10/714,225

(22) Filed: Nov. 14, 2003

(65) Prior Publication Data

US 2004/0097922 A1    May 20, 2004

Related U.S. Application Data

(60) Provisional application No. 60/426,439, filed on Nov. 14, 2002.

(51) Int. Cl.
*A61B 17/00* (2006.01)

(52) U.S. Cl.
USPC .......................................................... 606/54

(58) Field of Classification Search ............. 606/54–60, 606/103, 130; 318/560; 702/196; 345/644; 483/29; 600/426
See application file for complete search history.

(56) References Cited

U.S. PATENT DOCUMENTS

| | | | |
|---|---|---|---|
| 2,250,417 A * | 7/1941 | Ettinger | ........................ 606/59 |
| 3,727,610 A | 4/1973 | Riniker | |
| 4,308,863 A | 1/1982 | Fischer | |
| 4,375,814 A | 3/1983 | Gourlandt | |
| 4,483,334 A | 11/1984 | Murray | |
| 4,502,473 A | 3/1985 | Harris et al. | |
| 4,570,625 A | 2/1986 | Harris et al. | |
| 4,621,627 A | 11/1986 | DeBastiani et al. | |
| 4,628,919 A | 12/1986 | Clyburn | |
| 4,680,628 A * | 7/1987 | Wojcik et al. | ................ 378/98.2 |
| 4,730,608 A | 3/1988 | Schlein | |
| 4,895,141 A | 1/1990 | Koeneman et al. | |
| 4,922,896 A | 5/1990 | Agee et al. | |
| 4,973,331 A | 11/1990 | Pursley et al. | |
| 4,991,579 A | 2/1991 | Allen | |

(Continued)

FOREIGN PATENT DOCUMENTS

| | | |
|---|---|---|
| DE | 10129942 | 2/2002 |
| EP | 0314021 | 5/1989 |

(Continued)

OTHER PUBLICATIONS

International Search Report, PCT/US03/29435, Nov. 16, 2004.

(Continued)

*Primary Examiner* — Kevin T Truong
*Assistant Examiner* — Christian Sevilla
(74) *Attorney, Agent, or Firm* — Haynes and Boone, LLP

(57) ABSTRACT

A method for determining the proper configuration of a fixator or other medical device to correct a given deformity by solving the simultaneous equations representing the kinematic chain for the device. One skilled in the art would appreciate that x-rays, clinical evaluations, or a combination of both may be used to determine the distal and proximal mounting characteristics, including the use of digital x-rays with images from an imaging device to reduce or eliminate the needs for a physician to take measurements. The technique can be expanded to other medical evaluations. Additionally, one skilled in the art would appreciate that the method of the present invention could be written as one or more sets of instructions stored on a computer-readable medium that could be executed by a computer.

17 Claims, 20 Drawing Sheets

U.S. PATENT DOCUMENTS

| | | | |
|---|---|---|---|
| 5,019,077 A | 5/1991 | De Bastiani et al. | |
| 5,074,866 A | 12/1991 | Sherman et al. | |
| 5,160,335 A | 11/1992 | Wagenknecht | |
| 5,207,676 A | 5/1993 | Canadell et al. | |
| 5,314,426 A | 5/1994 | Pohl et al. | |
| 5,393,161 A | 2/1995 | Mata et al. | |
| 5,429,637 A | 7/1995 | Hardy | |
| 5,437,667 A | 8/1995 | Papierski et al. | |
| 5,454,810 A | 10/1995 | Pohl et al. | |
| 5,501,684 A | 3/1996 | Schlapfer et al. | |
| 5,545,162 A | 8/1996 | Huebner | |
| 5,601,551 A | 2/1997 | Taylor et al. | |
| 5,653,707 A | 8/1997 | Taylor et al. | |
| 5,658,283 A | 8/1997 | Huebner | |
| 5,662,651 A | 9/1997 | Tornier et al. | |
| 5,683,389 A | 11/1997 | Orsak | |
| 5,688,271 A | 11/1997 | Faccioli et al. | |
| 5,690,633 A | 11/1997 | Taylor et al. | |
| 5,702,389 A | 12/1997 | Taylor et al. | |
| 5,713,357 A * | 2/1998 | Meulenbrugge et al. | 600/411 |
| 5,728,095 A * | 3/1998 | Taylor et al. | 606/54 |
| 5,738,684 A | 4/1998 | Thomas et al. | |
| 5,746,741 A | 5/1998 | Kraus et al. | |
| 5,752,954 A | 5/1998 | Mata et al. | |
| 5,776,132 A | 7/1998 | Blyakher | |
| 5,788,695 A | 8/1998 | Richardson | |
| 5,803,924 A | 9/1998 | Oni et al. | |
| 5,843,081 A | 12/1998 | Richardson | |
| 5,846,245 A | 12/1998 | McCarthy et al. | |
| 5,891,144 A | 4/1999 | Mata et al. | |
| 5,897,555 A | 4/1999 | Clyburn et al. | |
| 5,928,230 A | 7/1999 | Tosic | |
| 5,941,879 A | 8/1999 | Walulik et al. | |
| 5,944,719 A | 8/1999 | Leban | |
| 5,951,475 A | 9/1999 | Gueziec et al. | |
| 5,951,556 A | 9/1999 | Faccioli et al. | |
| 5,961,515 A | 10/1999 | Taylor et al. | |
| 5,971,984 A | 10/1999 | Taylor et al. | |
| 5,976,133 A | 11/1999 | Kraus et al. | |
| 5,976,134 A | 11/1999 | Huebner | |
| 6,017,341 A | 1/2000 | Windhagen et al. | |
| 6,023,850 A * | 2/2000 | Trapet | 33/502 |
| 6,030,386 A | 2/2000 | Taylor et al. | |
| 6,036,691 A | 3/2000 | Richardson | |
| 6,056,748 A | 5/2000 | Weiner | |
| 6,080,153 A | 6/2000 | Mata et al. | |
| 6,102,911 A | 8/2000 | Faccioli et al. | |
| 6,129,727 A | 10/2000 | Austin et al. | |
| 6,146,390 A | 11/2000 | Heilbrun et al. | |
| 6,162,224 A | 12/2000 | Huebner | |
| 6,171,308 B1 | 1/2001 | Bailey et al. | |
| 6,171,309 B1 | 1/2001 | Huebner | |
| 6,176,860 B1 | 1/2001 | Howard | |
| 6,200,317 B1 | 3/2001 | Aalsma et al. | |
| 6,245,071 B1 | 6/2001 | Pierson | |
| 6,277,118 B1 | 8/2001 | Grant et al. | |
| 6,277,119 B1 | 8/2001 | Walulik et al. | |
| 6,340,361 B1 | 1/2002 | Kraus et al. | |
| 6,348,053 B1 | 2/2002 | Cachia | |
| 6,461,358 B1 | 10/2002 | Faccioli et al. | |
| 6,491,694 B1 | 12/2002 | Orsak | |
| 6,514,254 B1 | 2/2003 | Falls | |
| 6,520,961 B1 | 2/2003 | Marsh | |
| 7,282,052 B2 | 10/2007 | Mullaney | |
| 2002/0147455 A1 | 10/2002 | Carson et al. | |
| 2007/0282338 A1 | 12/2007 | Mullaney | |

FOREIGN PATENT DOCUMENTS

| | | |
|---|---|---|
| GB | 2110094 | 6/1983 |
| WO | WO-02/094112 | 11/2002 |
| WO | 03/086213 A2 | 10/2003 |

OTHER PUBLICATIONS

International Search Report, PCT/US03/36590, Nov. 19, 2004.

European Patent Office, Communication transmitting European search report dated Jul. 28, 2010, Application No. 03811627.3-2310/1567046 PCT/US0336590, 5 pages.

Canadian Patent Office, Office Action dated Oct. 28, 2010, Application No. 03811627.3-2310/1567046, 2 pages.

* cited by examiner

410

420

430

440

1600

METHOD FOR USING A FIXATOR DEVICE

STATEMENT OF RELATED PATENT APPLICATIONS

This non-provisional patent application claims priority under 35 U.S.C. §119 to U.S. Provisional Patent Application No. 60/426,439, titled Unilateral Fixator Method, filed Nov. 14, 2002. This provisional application is hereby fully incorporated herein by reference.

FIELD OF THE INVENTION

The present invention relates to a method for using a fixator device and more specifically to developing a prescription for adjusting a fixator for deformity correction and for characterizing tissue through non-evasive methods.

BACKGROUND OF THE INVENTION

In orthopedic medicine, physicians often need to correct certain skeletal injuries or deformities with external fixator devices. These devices use pins or wires attached to the separate bone segments and an external structural frame to align, or fix, the bone segments in a way to aid in repairing the injury or correcting the deformity. Often the physician must gradually adjust the orientation of the bone segments over time, optimally with the capability to adjust the orientation along six degrees of freedom to ensure the bone segments are placed in the correct anatomic condition.

Devices and methods for treating musculoskeletal deformities are well known in the art. Although these devices vary considerably in design, they typically fall into two broad categories, circular ring and unilateral devices. The circular ring device category is exemplified by Ilizarov-type systems, which have two rings connected by linear struts with a fixed or hinged connection at each end of each strut. A device called a space frame, which has two rings connected by six linear struts having a spherical joint at each end arranged in a hexapod configuration, e.g., a Stewart frame, represents an advancement on the original Ilizarov concept.

The Ilizarov device is constructed based on the deformity that needs correcting, that is, for a specific patient and a specific deformity on that patient, hinges and struts are added to address each degree of deformity in a specific case. Ilizarov-type devices are often referred to as serial manipulators in that each adjustment relates to a single degree of deformity. This approach requires the frame to be constructed based on the deformity present, resulting in a fairly straightforward method of use but a potentially complex set of multiple and potentially endless configurations. The space frame is a device that conceptually comes in one configuration even though rings and struts can be of differing sizes. The Stewart frame-type space frame is often referred to as a parallel manipulator in that any given adjustment to any of the six struts will result in a change to all six degrees of freedom. This characteristic makes the Stewart-frame type device less intuitive to use and a computer program is often required to direct the user in making the adjustments to correct the deformity.

The unilateral device category has several devices that basically consist of a series of orthogonal planar hinges or spherical joints and, in some cases, sliders that can be locked into a particular orientation. Typically these devices can be used to fix bone segments in a particular orientation but not to gradually adjust the orientation, since the joints of the device do not have a direct adjustment device associated with each hinge or slider. Instead, the joints of the device must be loosened and then grossly manipulated on the device as a whole. Like the Ilizarov-type circular ring fixators, these devices often need to be constructed or mounted in a particular orientation depending on the characterization of the deformity. This requirement complicates their use and also necessitates multiple configurations to address the range of deformities that physicians typically encounter.

An innovative unilateral fixator, described in U.S. Non-Provisional patent application Ser. No. 10/664,769, entitled Unilateral Fixator, incorporated herein by reference, provides a six-degree-of-freedom manipulator in the form of an open kinematic chain, similar to many industrial robot arms in use today. At the start of the kinematic chain is the connection to what would be the reference bone segment, otherwise known as the ground. At the end of the kinematic chain is the connection to what would be the moving bone segment. Each of the links in the kinematic chain is made up of a rigid structural member with the connection between links being the joints.

The positioning and adjusting of a fixator, such as a six-degrees-of-freedom unilateral fixator described in U.S. Non-Provisional patent application Ser. No. 10/664,769 allows a physician to correct a deformity. The starting point for determining the positioning and adjusting of the fixator includes x-rays that depict a given deformity. Typically, measurements such as the axial rotation, the anterior-posterior (AP) rotation, the lateral rotation, the pin offset, and bone length, are used to position and adjust a fixator. A physician may make these measurements directly on x-rays of a deformity. Although this technique is adequate for characterizing a deformity, these manual measurements do require increased work for a physician and may introduce error. An improved method would take advantage of digital imaging to reduce or eliminate the need for manual measurements.

What is needed is a method of deformity characterization and description of the relative mounting orientation of a deformity-correcting fixator device relative to the deformity such that a mathematical transform can be obtained is needed. Optimally, the method would minimize measurements taken by a physician. Also, the method may be adaptable to characterizing any type of tissue configuration captured on an x-ray.

SUMMARY OF THE INVENTION

The present invention provides a method for transforming readily available orthopedic data into parameters to configure a fixator to achieve a needed or desired orientation of the bone segments, by solving a system of simultaneous equations represented by a kinematic chain for a fixator device that provides six degrees of freedom of movement, either an open kinematic or closed kinematic chain. Advantageously, this system provides a method for manipulating a fixator with six degrees of freedom that can correct, through both gross and fine adjustments, bone deformities in any direction. One aspect of the invention includes a method for extracting data from an x-ray that greatly reduces or eliminates the need for a physician to perform manual measurements.

One aspect of the present invention provides a method for determining a position of a deformity-correcting fixator. The steps of the method include (1) characterizing a mounting condition for a proximal bone fragment attachment apparatus and a distal bone fragment attachment apparatus; (2) determining a first set of fixator settings and characteristics corresponding to the physical orientation and characteristics of the fixator; (3) determining a deformity correction matrix by solving a plurality of simultaneous equations corresponding to kinematic equations for the fixator; and (4) solving for a second set of fixator settings by equating the deformity correction matrix to a deformity correction transform. In this aspect, the mounting conditions may be characterized using manual measurements.

In another aspect of the invention, an imaging device may be used to place an image on at least two digital x-rays to characterize tissue captured in the x-ray, including the steps of (1) projecting an image from an imaging device onto an x-ray, wherein the x-ray contains the tissue and the imaging device includes at least three balls; (2) generating a digital computer-readable file of the x-ray; (3) detecting the edge of images on the digital file of the x-ray; (4) discovering possible circular outlines from images; (5) determining the radius and center associated with the possible circular outlines; (6) determining one or more anatomical axes associated with the tissue; (7) characterizing the coordinate system associated with the imaging device; and (8) characterizing the physical configuration of the tissue. In one exemplary embodiment, the tissue represents bone fragments to be corrected by a fixator. This aspect can be used to replace manual measurements for characterizing mounting conditions of a fixator.

The aspects of the present invention may be more clearly understood and appreciated from a review of the following detailed description of the disclosed embodiments and by reference to the drawings and claims.

DETAILED DESCRIPTION OF EXEMPLARY EMBODIMENTS

Exemplary embodiments of the present invention provide a method for defining the manipulation of a fixator device and for characterizing tissue, such as bone fragments, which may be acted upon by the fixator.

Figure 1:
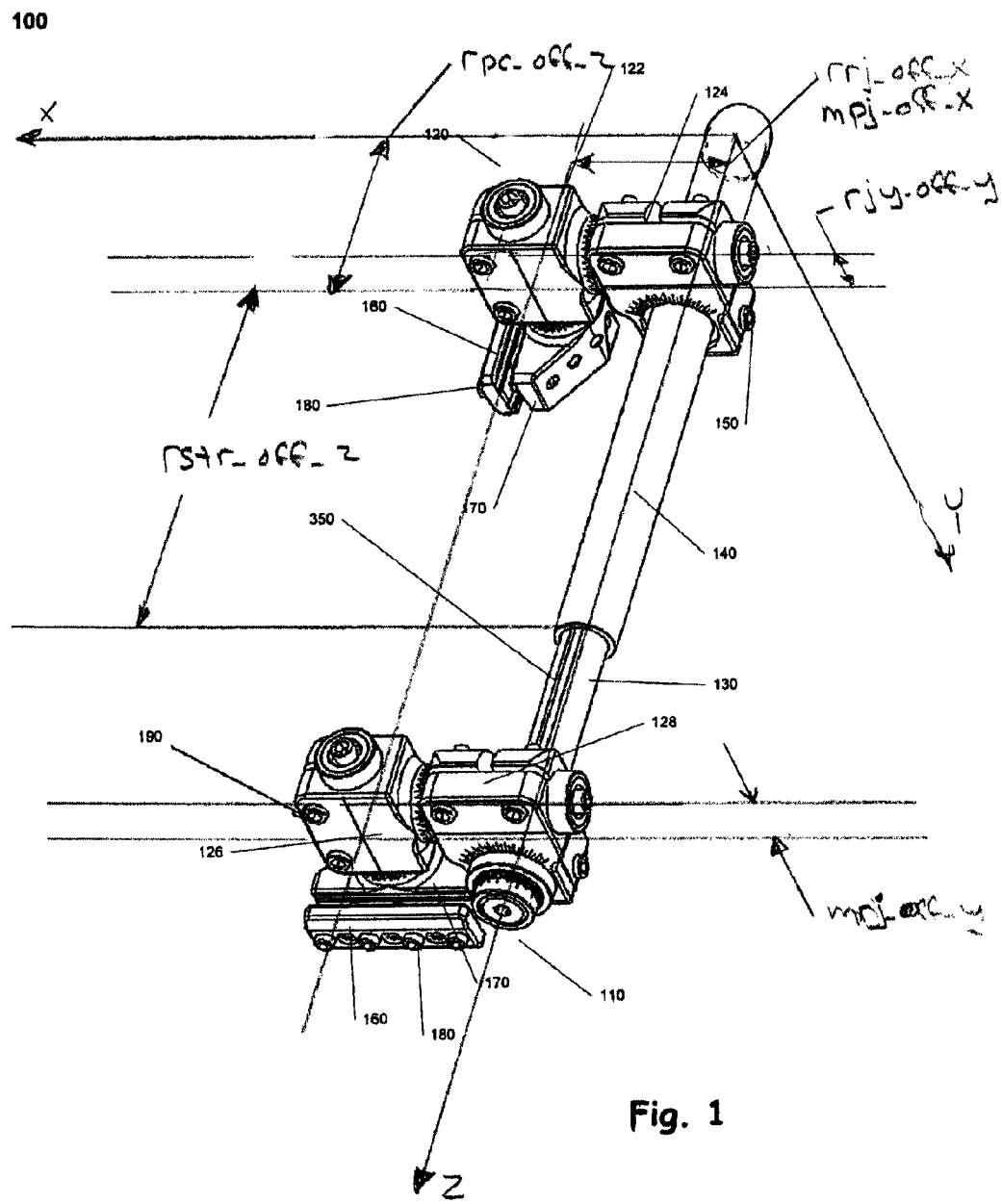
FIG. 1 provides an image of an exemplary unilateral fixator.

FIG. 1 provides an isomeric image of an exemplary unilateral fixator 100 that may be manipulated using the method of the present invention. Referring to FIG. 1a first compound movable joint 110, or bone fragment attachment apparatus, is attached to an extension strut 130 and a second compound movable joint 120, or bone fragment attachment apparatus, is attached to a base strut 140. These two compound movable joints 110, 120 are identical. The first compound movable joint 110 and second compound movable joint 120 each include two revolute joints 122, 124, 126, 128, the axes of which are orthogonally opposed. The second compound movable joint 120, also referred to herein as the ankle, is able to slide along, but not rotate about, the axis of the base strut 140. The first compound movable joint 110, also referred to herein as the wrist, is able to rotate about, but not slide along, the axis of the extension strut 130. Both the ankle 120 and the wrist 110 can be locked in place on their respective struts 130, 140 by tightening a corresponding cap screw, such as cap screw 150. Similarly, revolute joints 122, 124, 126, 128 of the wrist and ankle may be fixed into place with one or more screws 190.

Attached to each of the first and second compound moveable joint 110, 120 is a clamp plate 160 and a clamp body 170. These clamp plates 160 and clamp bodies 170 receive pins or other suitable devices for attaching the first and second compound moveable joints 110, 120 to a patient's body, and more specifically to segments of a bone (not shown). Each clamp plate 160 is secured to its corresponding clamp body 170 with a plurality of cap screws, such as screw 180. Each cap screw 180 may be threaded into a combination of holes in the clamp plate 160 and the clamp body 170 such that cap screws 180 straddle each pin.

One skilled in the art will appreciate that the exemplary method described below could be used for any deformity-correcting fixator that provides for six degrees of freedom, such as a ring fixator, and is not limited to the exemplary unilateral fixator presented in FIG. 1.

The current invention includes a method for translating clinical measurements into device parameters that establish the proper orientation of each segment revolute joint 122, 124, 126, 128 and the length of the strut structure. The fixator device is attached through pins and pin claps, or similar connecting structures, to two bone fragments that comprise the bone deformity. The device may then be manipulated, that is, moved, such that the bone fragments are aligned in a desired position. This alignment may be changed over time to complete the deformity correction process. One of the bone fragments will be a reference fragment. The other fragment, the moving fragment, will be moved to align with the reference fragment.

One skilled in the art will appreciate that the method of the present invention could be written as one or more sets of instructions stored on a computer-readable medium that could be executed by a computer. This computer may include a memory storage device; one or more computer processing units; input devices, such as a keyboard and pointing device such as a mouse; a monitor; and other peripheral devices.

Figure 2:
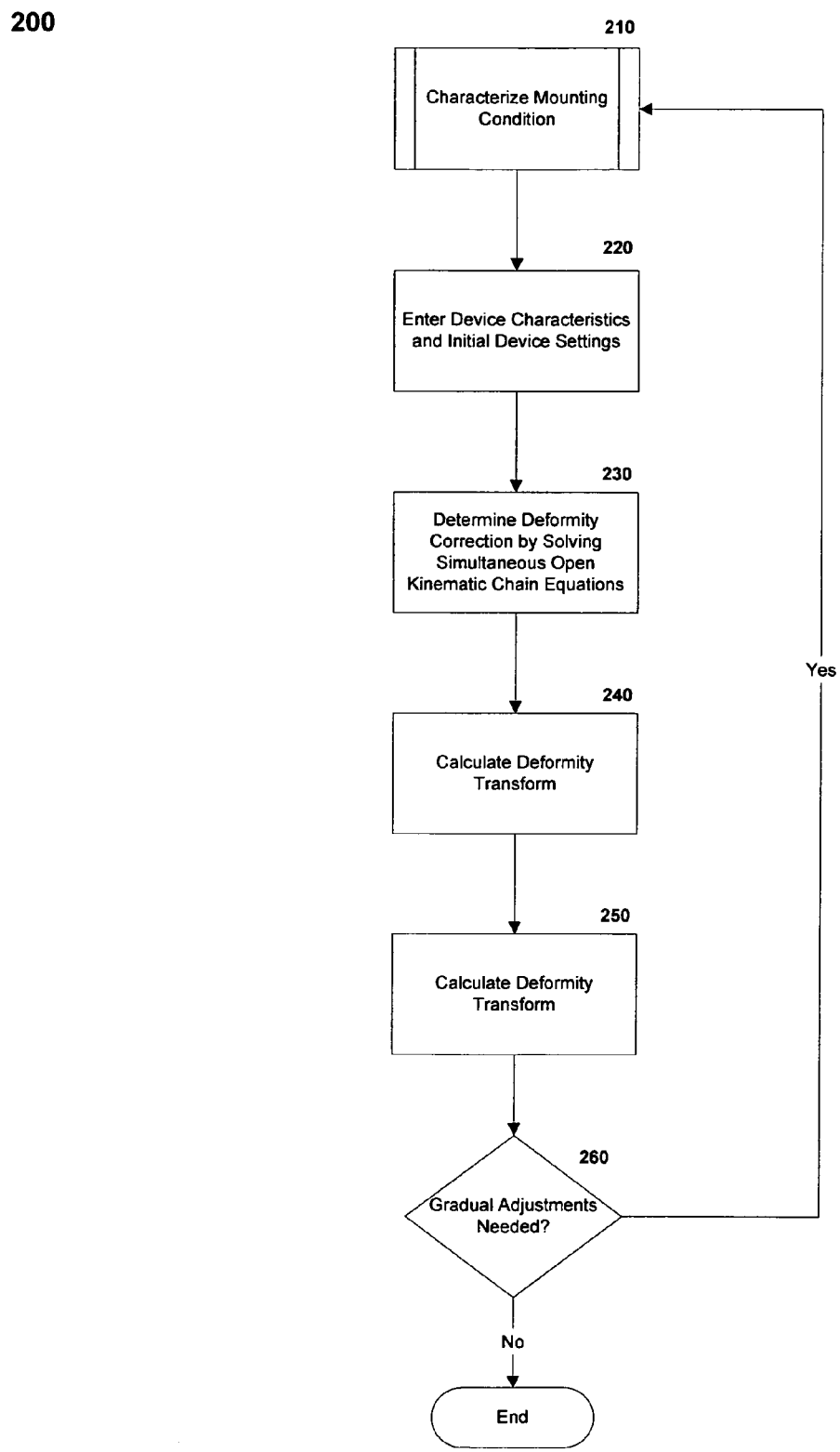
FIG. 2 presents a process flow diagram for an exemplary method for establishing the proper orientation of a fixator device of the present invention.

FIG. 2 presents a process flow diagram for an exemplary method 200 for establishing the proper orientation of a fixator device of the present invention. Referring to FIG. 2, at step 210, the mounting condition of the fixator in reference to the two bone fragments, the reference fragment and moving fragment, is characterized. For one embodiment, this step is discussed in greater detail below, in conjunction with FIG. 3. In a second embodiment, which employs the use of digital x-rays, this step is discussed in conjunction with FIG. 5.

At step 220, the physical characteristics and initial settings of the device are determined. These characteristics and settings comprise both fixed and variable input values. The fixed values relate to the hard dimensions of the fixator device, that is, values that are constant for a given fixator. The variable inputs are the settings of the adjustments of the device. The fixed values include the following (where the terms "reference" and "moving" refer to the bone fragment attached to the compound movable joint):

reference pin clamp offset in the Z axis (rpc_off_z)
    reference roll joint offset in the X axis (rrj_off_x)
    reference roll joint offset in the Z axis (rrj_off_z)
    reference yaw joint offset in the X axis (ryj_off_x)
    reference yaw joint offset in the Y axis (ryj_off_y)
    reference yaw joint offset in the Z axis (ryj_off_z)
    reference strut offset in the X axis (rstr_off_x)
    reference strut offset in the Z axis (rstr_off_z)
    moving strut offset in the X axis (mstr_off_x)
    moving strut offset in the Y axis (mstr_off_y)
    moving strut offset in the Z axis (mstr_off_z)
    moving roll joint offset in the X axis (mdj_off_x)
    moving roll joint offset in the Y axis (mrj_off_y)
    moving roll joint offset in the Z axis (mrj_off_z)
    moving pitch joint offset in the X axis (mpj_off_x)
    moving pitch joint offset in the Y axis (mpj_off_y)
    moving pitch joint offset in the Z axis (mpj_off_z)

The variable values, which are solved for in the manipulation calculation process, include the following (where the terms "reference" and "moving" refer to the bone fragment attached to the compound movable joint):

initial reference roll joint rotation ($rrj\_rot_{initial}$)
    initial reference pitch joint rotation ($rpj\_rot_{initial}$)
    initial reference yaw joint rotation ($ryj\_rot_{initial}$)
    initial reference strut offset in the Y axis ($rstr\_off\_y_{initial}$)
    initial moving roll joint rotation ($mrj\_rot_{initial}$)
    initial moving pitch joint rotation ($mpj\_rot_{initial}$)

At step 230, the deformity correction is determined. This determination is based on successive solving of the simultaneous equations comprising the kinematic chain equations for a fixator device. The five equations related to an exemplary embodiment are provided below, along with the definition of the matrixes that form the equation variables. Some of the variables are described below, in connection with FIG. 3.

$$A = M_{asc\_rf\_axial\_rot} \cdot M_{asc\_rf\_ap\_rot} \cdot M_{asc\_rf\_pin\_off} \cdot M_{asc\_rf\_lat\_rot}$$

$$B = M_{asc\_rpc\_off} \cdot M_{asc\_rj\_rot} \cdot M_{asc\_rrj\_off} \cdot M_{asc\_rrj\_rot} \cdot M_{asc\_ryj\_off}$$

$$C = M_{asc\_ryj\_rot} \cdot M_{asc\_rstr\_off} \cdot M_{asc\_mstr\_off} \cdot M_{asc\_mjr\_rot}$$

$$D = M_{asc\_mjr\_off} \cdot M_{asc\_mpj\_rot} \cdot M_{asc\_mpj\_off} \cdot M_{asc\_mf\_lat\_rot}$$

$$E = M_{asc\_mf\_pin\_off} \cdot M_{asc\_mf\_ap\_rot} \cdot M_{asc\_mf\_axail\_rot}$$

where, $$M_{asc\_rf\_axial\_rot} = \begin{bmatrix} \cos(rf\_axial\_rot) & 0 & \sin(rf\_axial\_rot) & 0 \\ 0 & 1 & 0 & 0 \\ -\sin(rf\_axial\_rot) & 0 & \cos(rf\_axial\_rot) & 0 \\ 0 & 0 & 0 & 1 \end{bmatrix}$$

$$M_{asc\_rf\_ap\_rot} = \begin{bmatrix} \cos(rf\_ap\_rot) & \sin(rf\_ap\_rot) & 0 & 0 \\ -\sin(rf\_ap\_rot) & \cos(rf\_ap\_rot) & 0 & 0 \\ 0 & 0 & 1 & 0 \\ 0 & 0 & 0 & 1 \end{bmatrix}$$

$$M_{asc\_rf\_pin\_off} = \begin{bmatrix} 1 & 0 & 0 & rf\_pin\_off\_x \\ 0 & 1 & 0 & rf\_pin\_off\_y \\ 0 & 0 & 1 & rf\_pin\_off\_z \\ 0 & 0 & 0 & 1 \end{bmatrix}$$

$$M_{asc\_rf\_lat\_rot} = \begin{bmatrix} 1 & 0 & 0 & 0 \\ 0 & \cos(rf\_lat\_rot) & -\sin(rf\_lat\_rot) & 0 \\ 0 & \sin(rf\_lat\_rot) & \cos(rf\_lat\_rot) & 0 \\ 0 & 0 & 0 & 1 \end{bmatrix}$$

$$M_{asc\_ryj\_rot} = \begin{bmatrix} \cos(ryj\_rot) & 0 & \sin(ryj\_rot) & 0 \\ 0 & 1 & 0 & 0 \\ -\sin(ryj\_rot) & 0 & \cos(ryj\_rot) & 0 \\ 0 & 0 & 0 & 1 \end{bmatrix}$$

-continued $$M_{asc\_rstr\_off} = \begin{bmatrix} 1 & 0 & 0 & 0 \\ 0 & 1 & 0 & rstr\_off\_y \\ 0 & 0 & 1 & 0 \\ 0 & 0 & 0 & 1 \end{bmatrix}$$

$$M_{asc\_mstr\_off} = \begin{bmatrix} 1 & 0 & 0 & mstr\_off\_x \\ 0 & 1 & 0 & mstr\_off\_y \\ 0 & 0 & 1 & mstr\_off\_z \\ 0 & 0 & 0 & 1 \end{bmatrix}$$

$$M_{asc\_mrj\_rot} = \begin{bmatrix} \cos(mrj\_rot) & \sin(mrj\_rot) & 0 & 0 \\ -\sin(mrj\_rot) & \cos(mrj\_rot) & 0 & 0 \\ 0 & 0 & 1 & 0 \\ 0 & 0 & 0 & 1 \end{bmatrix}$$

$$M_{asc\_mrj\_off} = \begin{bmatrix} 1 & 0 & 0 & mrj\_off\_x \\ 0 & 1 & 0 & mrj\_off\_y \\ 0 & 0 & 1 & mrj\_off\_z \\ 0 & 0 & 0 & 1 \end{bmatrix}$$

$$M_{asc\_mpj\_rot} = \begin{bmatrix} 1 & 0 & 0 & 0 \\ 0 & \cos(mpj\_rot) & -\sin(mpj\_rot) & 0 \\ 0 & \sin(mpj\_rot) & \cos(mpj\_rot) & 0 \\ 0 & 0 & 0 & 1 \end{bmatrix}$$

$$M_{asc\_mpj\_off} = \begin{bmatrix} 1 & 0 & 0 & mpj\_off\_x \\ 0 & 1 & 0 & mpj\_off\_y \\ 0 & 0 & 1 & mpj\_off\_z \\ 0 & 0 & 0 & 1 \end{bmatrix}$$

$$M_{asc\_mf\_pin\_off} = \begin{bmatrix} 1 & 0 & 0 & 0 \\ 0 & \cos(mf\_lat\_rot) & -\sin(mf\_lat\_rot) & 0 \\ 0 & \sin(mf\_lat\_rot) & \cos(mf\_lat\_rot) & 0 \\ 0 & 0 & 0 & 1 \end{bmatrix}$$

$$M_{asc\_mf\_pin\_off} = \begin{bmatrix} 1 & 0 & 0 & mf\_pin\_off\_x \\ 0 & 1 & 0 & mf\_pin\_off\_y \\ 0 & 0 & 1 & mf\_pin\_off\_z \\ 0 & 0 & 0 & 1 \end{bmatrix}$$

$$M_{asc\_mf\_ap\_rot} = \begin{bmatrix} \cos(mf\_ap\_rot) & \sin(mf\_ap\_rot) & 0 & 0 \\ -\sin(mf\_ap\_rot) & \cos(mf\_ap\_rot) & 0 & 0 \\ 0 & 0 & 1 & 0 \\ 0 & 0 & 0 & 1 \end{bmatrix}$$

$$M_{asc\_mf\_axial\_rot} = \begin{bmatrix} \cos(mf\_axial\_rot) & 0 & \sin(mf\_axial\_rot) & 0 \\ 0 & 1 & 0 & 0 \\ -\sin(mf\_axial\_rot) & 0 & \cos(mf\_axial\_rot) & 0 \\ 0 & 0 & 0 & 1 \end{bmatrix}$$

At step 240, a deformity transform is calculated. This transform equates the solution to the kinematic chain equations to a desired deformity matrix, allowing for the solution of the variables associated with each of the revolute joints 122, 124, 126, 128 in the exemplary fixator. The following equation is used:

$$A \cdot B \cdot C \cdot D \cdot E = \begin{bmatrix} 1 & 0 & 0 & 0 \\ 0 & 1 & 0 & -bone\_length \\ 0 & 0 & 1 & 0 \\ 0 & 0 & 0 & 1 \end{bmatrix}$$

In other words, the product of the five matrixes represented by the designations A, B, C, D, and E, presented above, is set equal to the desired deformity transform. The deformity transform presented above is an augmented identity matrix. One skilled in the art would appreciate that the desired deformity matrix does not have to be an augmented identity matrix. Instead, the desired deformity transform can include a prescribed residual deformity.

At step 250, the fixator device position is set, based on the solution for the set of variable values at step 240. At step 260, if adjustments over time are needed, the process 200 returns to step 210 and repeats. In this case, the "initial device settings" at step 220 are the current settings for the device, that is, the settings determined at step 250. When no additional adjustments are needed, the process 200 ends.

Figure 3:
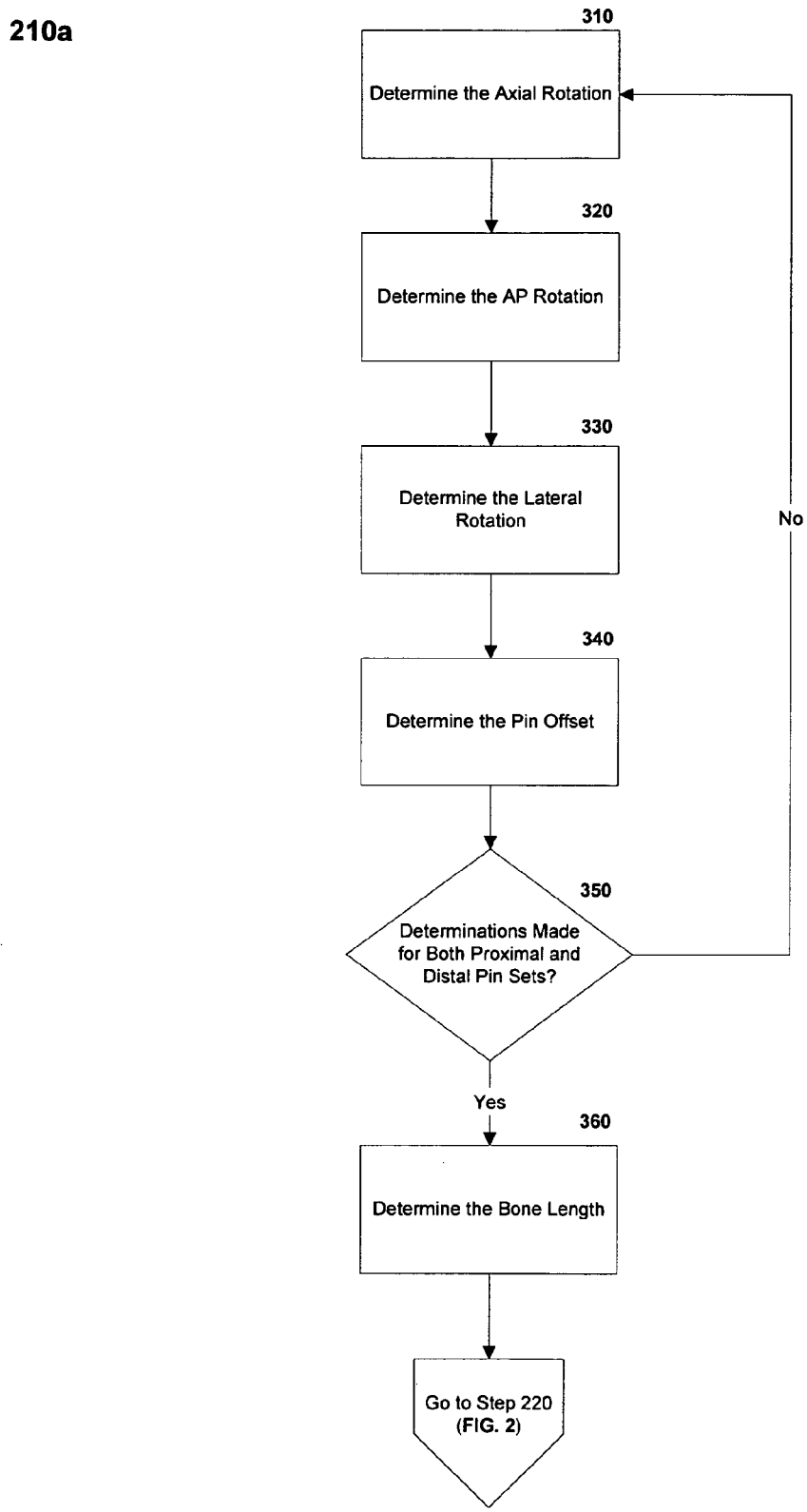
FIG. 3 provides a flow diagram for a process for characterizing the mounting conditions for an exemplary fixator in accordance with an exemplary embodiment of the present invention.
Figure 4A:
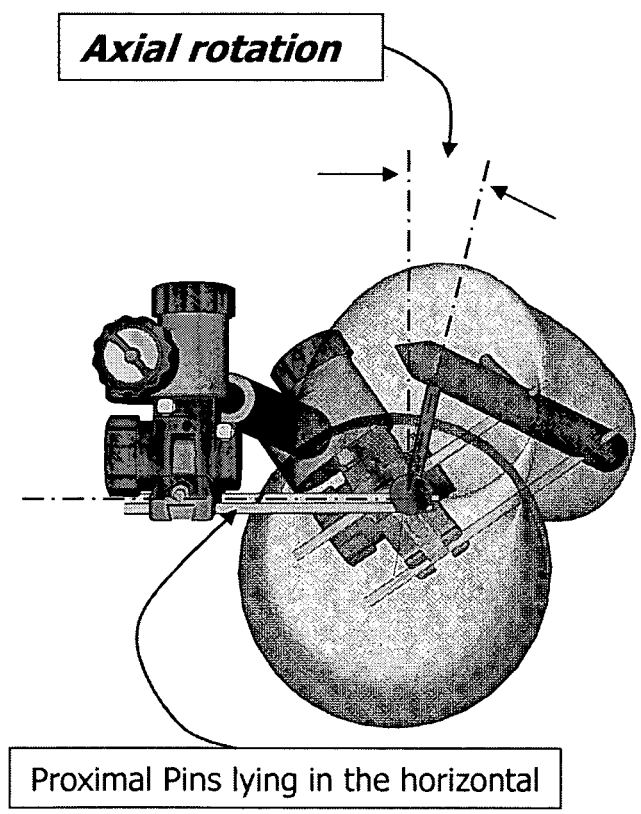
FIG. 4a provides an image of the axial rotation for an exemplary embodiment of the present invention.
Figure 4B:
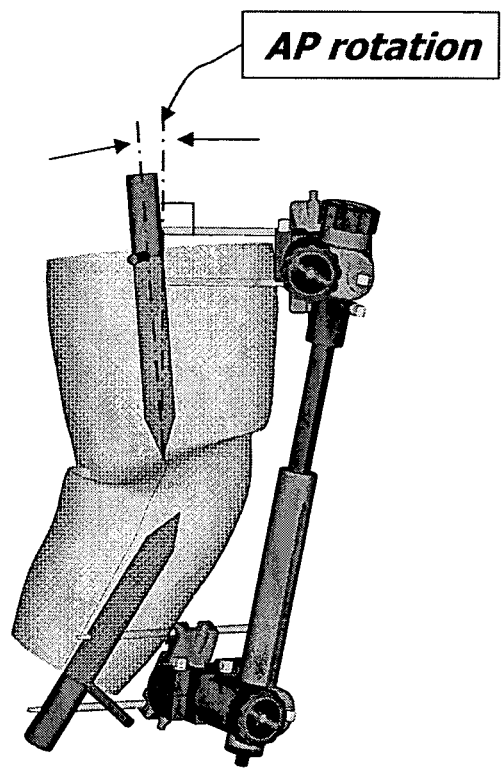
FIG. 4b provides an image of the axial rotation for an exemplary embodiment of the present invention.
Figure 4C:
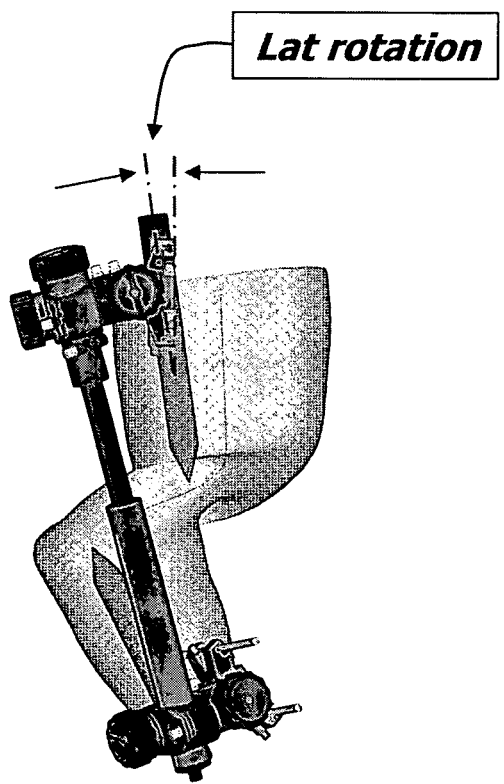
FIG. 4c provides an image of the axial rotation for an exemplary embodiment of the present invention.
Figure 4D:
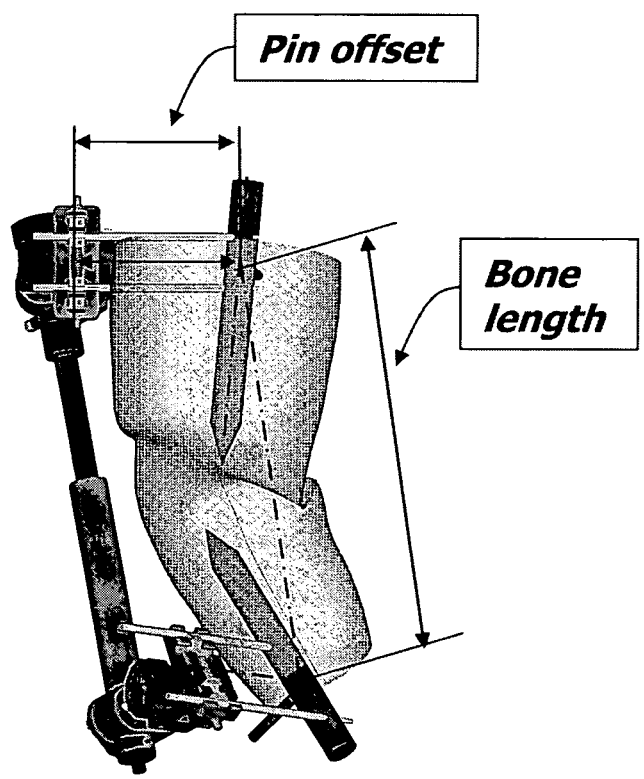
FIG. 4d provides an image of the axial rotation for an exemplary embodiment of the present invention.

FIG. 3 provides a flow diagram for a process 210*a*, and exemplary embodiment of step 210 in FIG. 2, for characterizing the mounting conditions for a fixator in accordance with an exemplary embodiment of the present invention. The process 210*a* of FIG. 3 is explained with reference to FIGS. 4*a* through 4*d*. FIG. 4*a* provides an image 410 of the axial rotation for an exemplary embodiment of the present invention. FIG. 4*b* provides an image 420 of the anterior-posterior (AP) rotation for an exemplary embodiment of the present invention. FIG. 4*c* provides an image 430 of the lateral rotation for an exemplary embodiment of the present invention. FIG. 4*d* provides an image 440 of the pin offset and bone length for an exemplary embodiment of the present invention. Returning to FIG. 3, at step 310, a determination is made of the axial rotation for the proximal pin set. With the proximal pins lying in a horizontal position, the magnitude of the axial rotation is observed with respect to the vertical. Image 410 depicts this measurement.

At step 320, the AP rotation for the proximal pins is determined. With the proximal pins lying in a plane parallel to the view plane, the magnitude of the AP rotation for the proximal mounting is observed with respect to the proximal fragment anatomic axis and a line normal to the proximal pins. Image 420 depicts this measurement.

At step 330, the lateral (lat) rotation for the proximal pins is determined. With the face plane of the proximal clamp assembly normal to the view plane, the magnitude of the lateral rotation for the proximal mounting is observed. Image 430 depicts this measurement.

At step 340, the proximal pin offset is determined. With the face plane of the proximal clamp assembly normal to the view plane, the pin offset is measured from the center of the proximal clamp assembly to the anatomic axis of the fragment attached to the proximal pin set. Image 440 depicts this measurement.

At step 350, the process 210*a* determines If the characterization of mounting conditions has been done for both the proximal and distal pin sets. If not, the process 210*a* returns to step 310 and is repeated through step 340. When, at step 350, it is determined that the mounting conditions for both the distal and proximal pin sets have been completed, the process 210*a* proceeds to step 360.

At step 360, the bone length is determined. The bone length is the distance along the anatomic axis between the proximal and distal mounts. Image 440 depicts this measurement.

One skilled in the art would appreciate that the process could begin with the distal pin set and be repeated for the proximal pin set. Alternatively, the proximal and distal characterizations could take place at the same time. For example, at step 310, the axial rotation for both the distal and proximate pin sets could be determined prior to moving to step 320 and so on. Also, one skilled in the art would appreciate that the five characterizations performed for both the distal and proximal pin sets could be performed in any order.

Figure 5:
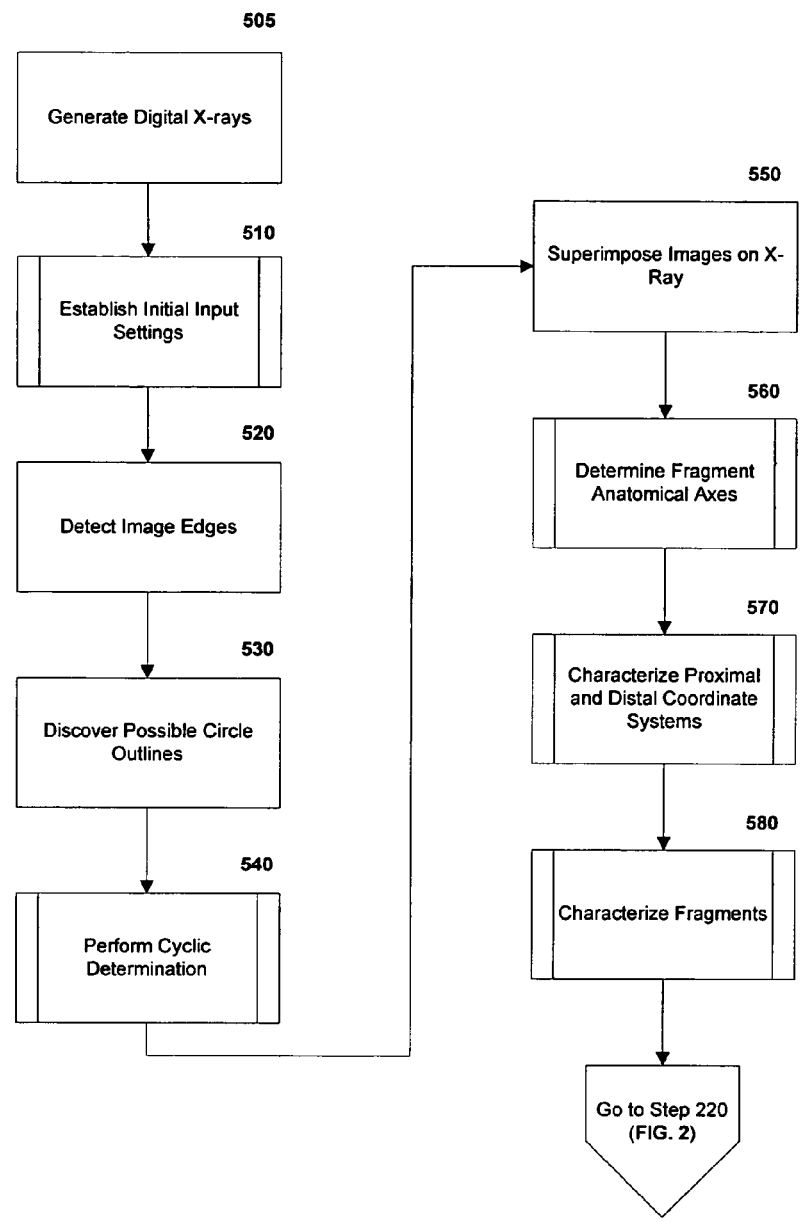
FIG. 5 provides a flow diagram for a process for characterizing the mounting conditions for an exemplary fixator in accordance with an alternative exemplary embodiment of the present invention.

FIG. 5 provides a flow diagram for a process 210*b*, and exemplary embodiment of step 210 in process 200, for characterizing the mounting conditions for an exemplary fixator in accordance with an exemplary embodiment of the present invention. In this exemplary embodiment, digital images of x-rays that depict the deformity and a fixator relative to the deformity are used to determine the mounting conditions of the fixator. This innovative technique for gathering data greatly reduces or eliminates the need for a physician to take physical measurements from the x-rays by projecting images, such as a set of orthogonal balls, on the x-rays that can be used to determine the required measurements.

Figure 16:
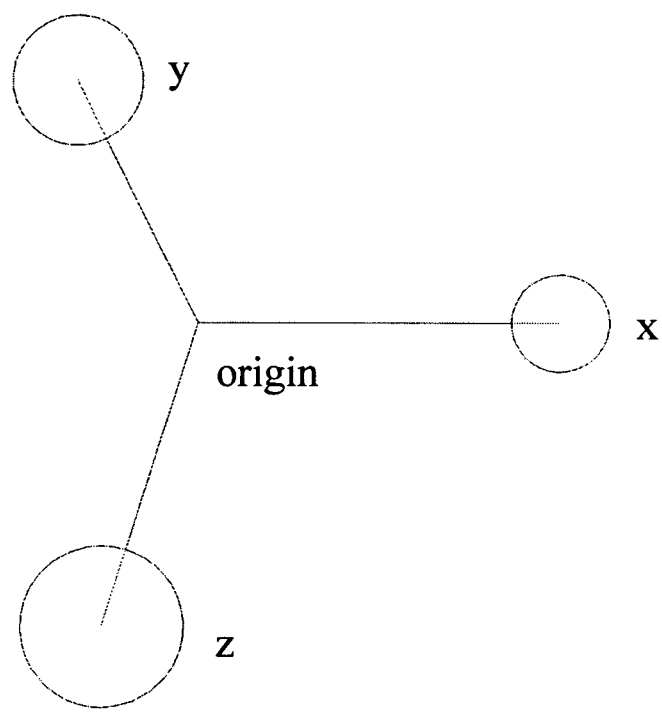
FIG. 16 provides a depiction of an axis system for a device used to project images on a digital image in accordance with an exemplary embodiment of the present invention.

Referring to FIGS. 1 and 5, at step 505 digital x-ray images are generated. To generate these x-ray images, AP and lateral x-rays are taken of a deformity, such as a bone fracture, and a fixator adjacent to the body section containing the deformity. The x-rays may be digital x-rays or a digital image may be taken of a film-based x-ray. An apparatus, also referred to herein as an imaging device, is attached between each pin clap body 170. An exemplary imaging device features a set of three posts with a sphere, or ball, mounted on one end of each post and the posts connected to each other at the other end of the posts and pin clamp plate 160. The posts may be orthogonal to each other. In this exemplary embodiment, the rods would be radiolucent to reduce the clutter in the x-ray image. The three balls of each apparatus are of varying size, for example 0.75 inches, 1.00 inches, and 1.25 inches. FIG. 16, described below, provides a conceptual image of an exemplary apparatus. The x-rays are taken and the images of the balls are projected onto the x-rays as circles.

One skilled in the art would appreciate that oblique x-rays, rather than AP and lateral x-rays could be taken. This different geometry would need to be considered in implementing the method as described below. Also, shapes other than spheres may be used in an imaging device or the shapes can be eliminated, with the ends of the posts serving as points that are located on the digital x-rays. The digital x-ray processing would then be altered to locate the projection of the used shape on the digital x-ray images.

The prior art includes a technique for employing stereoscopic infrared cameras to determine the location of a surgeon's instrument by including on that instrument three orthogonally-opposed posts with balls on each end and a fourth ball at the point where all three posts are joined. The present invention can be distinguished from this prior art. The prior art technique employs a computer-generated image of tissue that the surgeon is acting on. This image is based on typical parameters for a patient. Unlike the prior art technique, the present invention employs actual images of bone fragments, since "typical" fractures or deformities do not exist. Also, the surgical technique of the prior art relies on the reflectivity of the balls to infrared light to allow the imaging system to "see" the instrument as it moves. In the present invention, the balls are used to form images on a digital or digitized x-ray, or similar image of a fracture or deformity, or other tissue mass, to characterize the tissue mass based on the know configuration of the balls on the imaging device.

At step 510, initial input settings are established. At this step, the digital images of x-rays are read by a computer, the characteristics of the projected images are set, and digital image processing set-up is established. These processes provide input parameters used in the later evaluation of the x-ray images. This step is discussed in greater detail below, in conjunction with FIG. 6.

Figure 7:
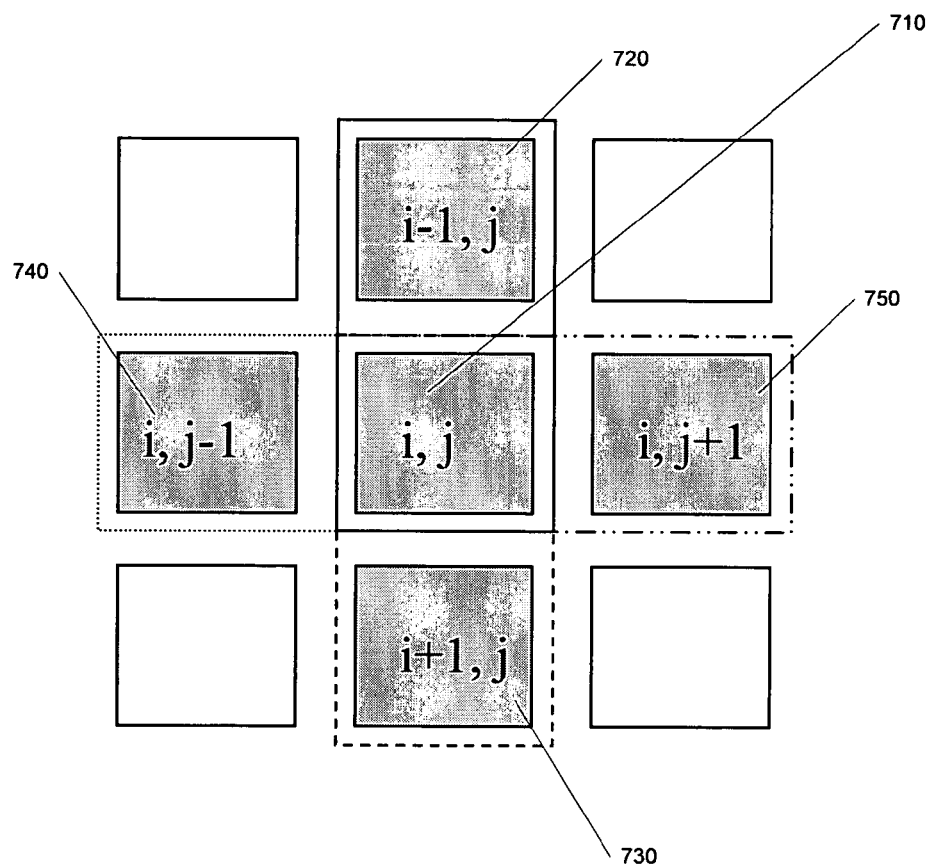
FIG. 7 provides a depiction of adjacent pixels in a digital image in accordance with an exemplary embodiment of the present invention.

At step 520, the edges of images on the digital x-rays are determined. That is, the edges for the individual shapes that make up the entire x-ray image are determined. These shapes may correspond to the imaging device, the fixator device, or the tissue, such as bone fragments. Each pixel within each of the x-ray bitmap images are evaluated with respect to the intensity values contained in adjacent pixels. If the ratio of the intensity of adjacent pixels is less than a specified slope value, then the pixel value is set to the maximum intensity (255). Conversely, if the ratio of the intensity of adjacent pixels is greater than a specified slope value, the pixel value is set to the minimum intensity (0). This process highlights the edges within the x-ray images, that is, maximizes the intensity of the edges of all images on the digital x-rays and minimizes the intensity of other parts of the image. FIG. 7 illustrates the relative position of pixels in an image. Pixel 710, labeled "i,j," is a pixel being evaluated. The intensity of pixel 710 is compared to the intensity of adjacent pixels 720, 730, 740, and 750 in the evaluation process. The process is repeated for all pixels in the bitmap image.

At step 530, possible circle outlines within the digital x-ray image are identified. In other words, each of the individual images that make up the entire x-ray image is evaluated to determine if that image represents a circle. In this exemplary embodiment, three balls of different size are attached to the end of three orthogonal segments to form a device used to project images onto the x-rays, an imaging device. One of these devices is attached to both the distal and the proximal ends of the exemplary unilateral fixator at the pin clamps. When x-rays from an x-ray source pass through the imaging device, circular shadows, or images, are generated on the overall x-ray image. The x-rays also pass through the soft and hard tissue, such as bone fragments, and, possibly, the fixator, and all of these structures may cause images to be formed on the overall x-ray image. The circular images can then be used to characterize the bone fragments or other tissue mass relative to the fixator device.

To scan the image for outlines that could represent the circular shadows of the balls representing the axis of the coordinate systems attached to each clamp assembly, an algorithm is used to step through an image matrix at a given increment. Each digital x-ray image is divided into a grid system of rows and columns. A starting point is selected as a central pixel from which a search is conducted in the horizontal and vertical direction to identify the next pixel having a maximum value (255). That is, the search attempts to identify the pixels the image edges, in the up, down, left and right direction. If the central pixel is itself at a maximum value (255), in other words, is on an edge, then that pixel is skipped. In addition, if while scanning in any given direction the number of pixels scanned over exceeds a maximum diameter setting for the circle being searched for, that central pixel is skipped. The maximum diameter is an input parameter to the process and represents the largest diameter a circular shadow corresponding to the imaging device may have on the digital x-ray image.

Figure 8:
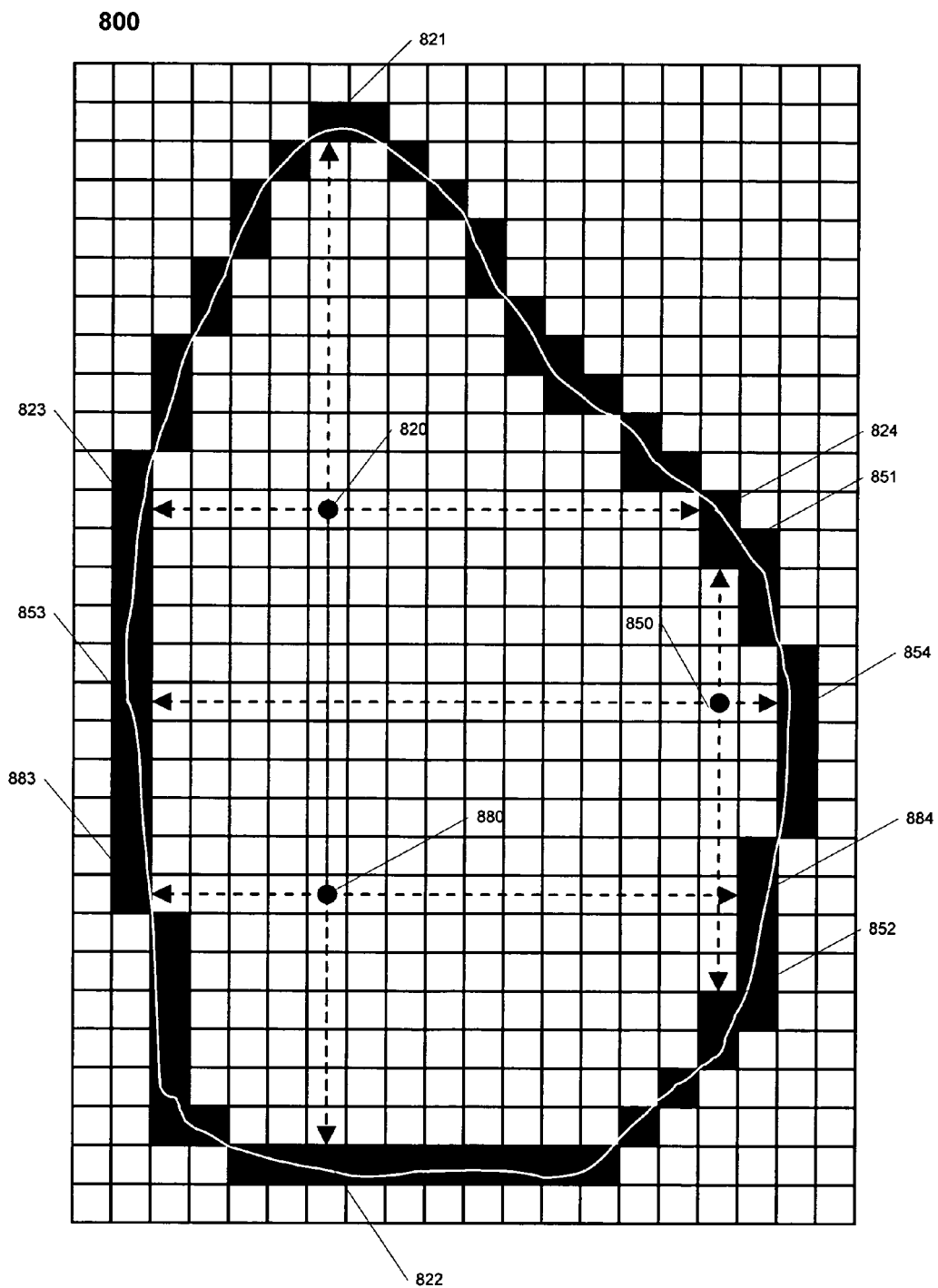
FIG. 8 provides a depiction of an edge image in a digital image in accordance with an exemplary embodiment of the present invention.

Each pixel of the digital x-ray image is scanned in sequence. This sequence may move horizontally or vertically along the digital x-ray image to consecutive pixels or may be random. Once the entire image is scanned, the central pixel locations along with the four pixels corresponding to the up, down, left and right edges for each central pixel are stored on a computer storage device in a table of values for each digital x-ray image. FIG. 8 illustrates this process for three central pixels 820, 850, 880. For central pixel 820, the up edge 821, down edge 822, left edge 823, and right edge 824 would be stored. Similarly, for central pixel 850, the up edge 851, down edge 852, left edge 853, and right edge 854 would be stored and for central pixel 880, the up edge 821, down edge 822, left edge 883, and right edge 884 would be stored. Note that the up edge and down edge pixels for central pixel 820 are identical to the up edge and down edge pixels for central pixel 880. This process is repeated for each available digital x-ray image.

At step 540, possible circular images are characterized, in terms of radius and center location. In other words, each individual images on the overall digital x-rays identified as possibly being a circular image corresponding to the projection of a ball on an imaging device, is evaluated to determine if the image is indeed a circle. This step is described in greater detail below, in conjunction with FIG. 9. One skilled in the art will recognize that, if other shapes are used on the imaging device, that is, shapes other than spheres, then geometric parameters that represent the specific shape used on the imaging device would be determined at step 540.

At step 550, the circular images identified at step 540 are superimposed onto the digital x-ray images. That is, the images calculated at step 540 are placed on the digital x-ray images by a computer. This process may include generating circles with the characteristics determined at step 540 on the digital x-ray image in a way that distinguishes these superimposed circular images from any original images on the overall digital x-ray image. This step is used to confirm that the circular images identified at step 540 represent the circular shadows on the x-rays of the balls that describe the imaging device attached to each pin clamp assembly.

At step 560, the anatomical axes of the bone fragments are determined. At step 570, the proximal and distal coordinate systems are characterized. The terms "proximal" and "distal" relate to the relative positions of the clamp assembles on the exemplary fixator. At step 580, the positions of the bone fragments are characterized. These steps are described in greater detail below, in association with FIGS. 14, 15, and 16, respectively.

Figure 6:
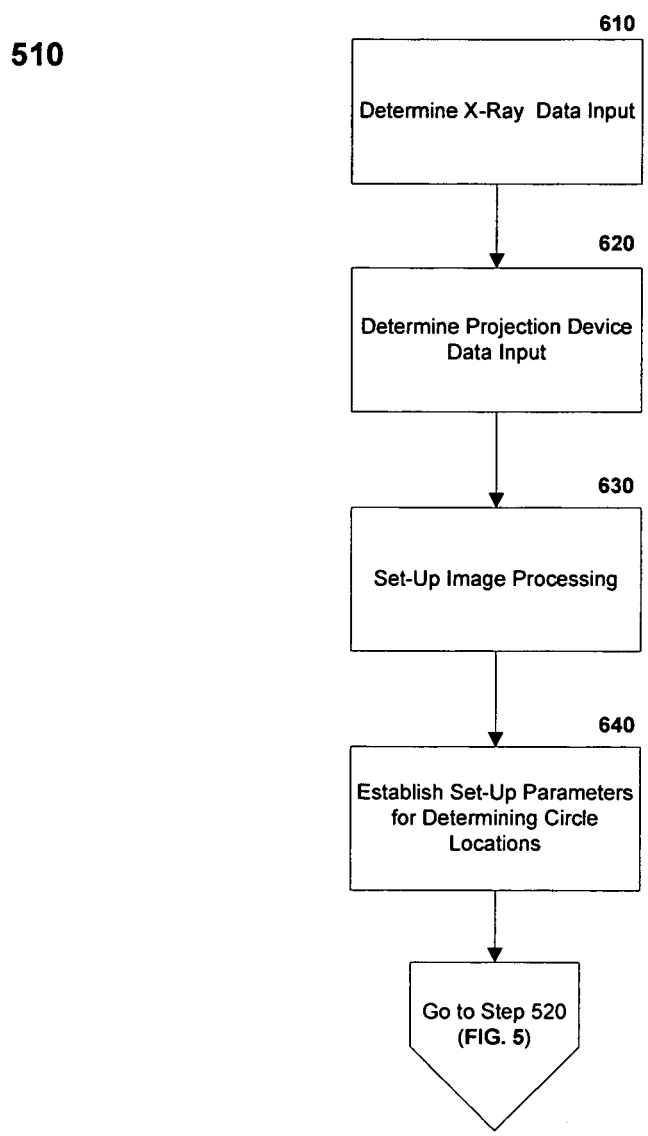
FIG. 6 provides a flow diagram for a process for establishing initial input parameters in accordance with an exemplary embodiment of the present invention.

FIG. 6 provides a flow diagram for a process 510 for establishing initial input parameters in accordance with an exemplary embodiment of the present invention. Referring to FIGS. 5 and 6, at step 610, the x-ray data input is determined. In this step, a bitmap or other type of digital image file for each x-ray taken may be read by a computer so that it may be acted upon by the exemplary embodiment of the present invention. The source of the data may be a file generated by a digital imaging x-ray machine or may be a file generated by digitizing an analog image, such as an x-ray film. Additional information used to evaluate the x-ray images may include the resolution, such as in dots per inch (DPI).

At step 620, the imaging device data input is determined. In this embodiment, the imaging device contains balls and rods. As discussed above, an exemplary device includes three balls, each rod having a ball attached to one end and with the other ends of the three rods joined together at a point referred to as the origin. One device is attached to each end of an exemplary fixator 100 (FIG. 1). Device data determined at step 620 include the distance between the ball centers and the origin.

One skilled in the art would appreciate that other device configurations may be used. One such configuration would include a fourth ball at the origin point, that is, the point where all three rods are joined. This configuration would allow the origin to be projected onto the x-ray image, simplifying the evaluation of the x-ray image, as discussed below. However, this configuration would also add an additional circular image on the x-ray, perhaps cluttering the overall digital x-ray image and making the identification of the individual circular images more difficult.

Similarly, one skilled in the art would appreciate that the two devices used in this example each could have different size balls, for a total of six different size balls, to facilitate discriminating between the circular images on the x-ray. Also, a single device could be used, attached to the fixator at a point. In this case, device input would also include the original settings of the fixator as aligned for the x-ray.

At step 630, the image processing set-up occurs. To facilitate the edge detection at step 520, the image contrast is increased. For example, a pixel with an intensity value that exceeds a threshold value, such as 155, would be increased to a value of 255, a maximum value. A pixel whose intensity does not exceed the threshold would have its intensity decreased by an order of magnitude. For example, a pixel with an intensity value of 100 would have the value decreased to a value of 10.

At step 640, set-up parameters for determining the location of circular images within the digital x-ray files are established. These parameters include the slope value used at step 520 to detect image edges, for example a value of 0.75, and minimum and maximum circle diameter values, used to filter circular images that would be too large or too small to represent the images generated from the projecting of the balls on the imaging device. Following this step, the process 510 moves to step 520 of process 210*b*.

Figure 9:
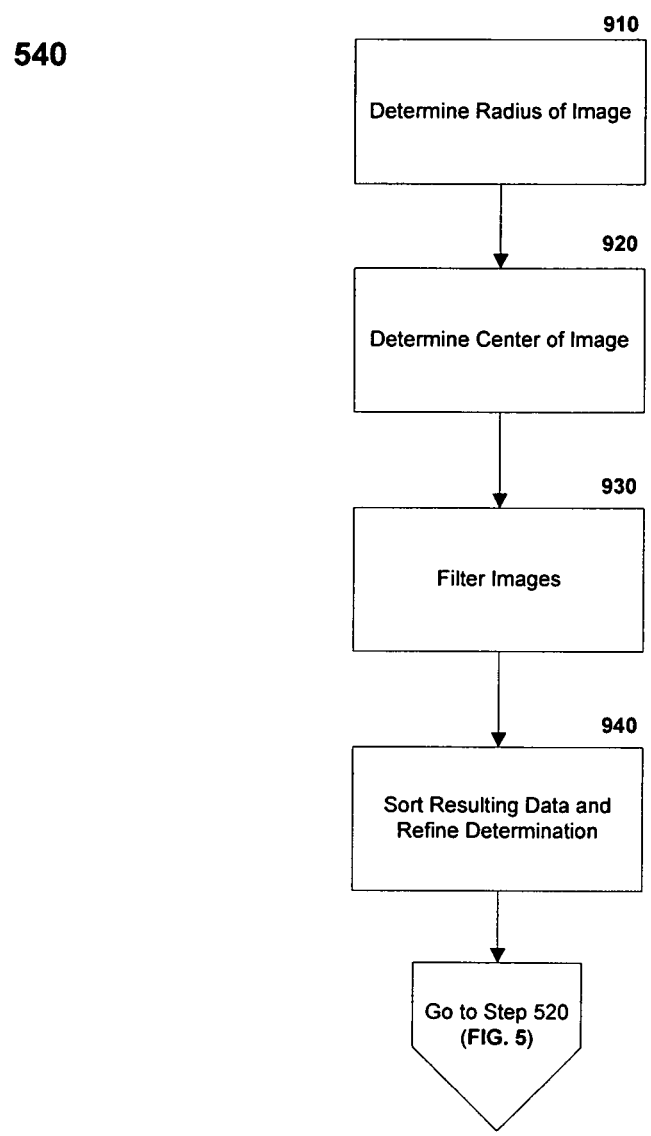
FIG. 9 provides a flow diagram for a process for characterizing circular images on a digital x-ray in accordance with an exemplary embodiment of the present invention.
Figure 10:
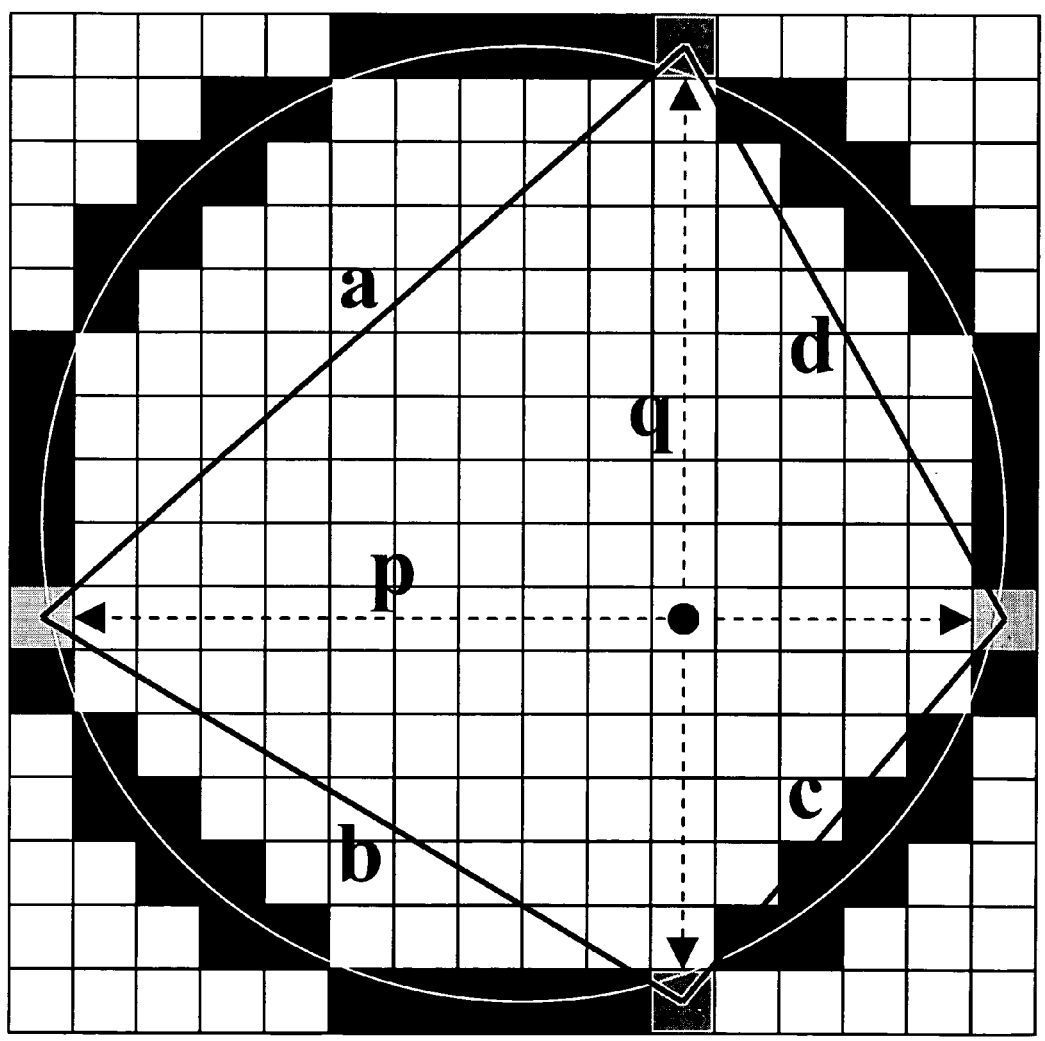
FIG. 10 provides a depiction of determining the circularity of an edge image in a digital image in accordance with an exemplary embodiment of the present invention.

FIG. 9 provides a flow diagram for a process 540 for performing cyclic determination in accordance with an exemplary embodiment of the present invention. Referring to FIGS. 5 and 9, at step 910, the radius for each possible circle outline identified at step 530 of process 210*b* is determined. As discussed above, in conjunction with step 530 of process 210*b* and illustrated in FIG. 8, sets of five points are collected, these five points representing a central pixel, up pixel, down pixel, left pixel, and right pixel point, where the up, down, left, and right points are on the edge of an image and the central point is located in the interior of that image. For each set of five points collected at step 530, a quadrilateral can be formed with consecutive sides "a," "b," "c," and "d" and main diagonals "p" and "q." FIG. 10 provides a graphical depiction of one of these quadrilaterals as would be the case for a circular outline, depicting sides "a," "b," "c," and "d" and main diagonals "p" and "q." Each set of five points is evaluated based on its degree of cyclicity in accordance with Ptolemy's theorem which states that a convex quadrilateral with consecutive sides "a," "b," "c," and "d" and diagonals "p" and "q" is cyclic if and only if the sum of the products of the lengths of opposite sides equals the product of the length of the diagonals. In other words, this relationship is described in the following equations, where the variables "a," "b," "c," "d," "p" and "q" are as represented in FIG. 10.

$$(a \cdot c) + (b \cdot d) = p \cdot q \quad \text{OR} \quad \frac{(a \cdot c) + (b \cdot d)}{p \cdot q} = 1$$

The closer the ratio of the sum of the products of the lengths of the opposite sides of the quadrilateral to the product of the lengths of the diagonals is 1, the more likely a circular shape passes through the four points of interest. As such, images determined at step 530 that do not reach a threshold value for cyclicity could be screened from further processing. Alternatively, all images can be further processed to confirm that they are or are not circular images.

Figure 11A:
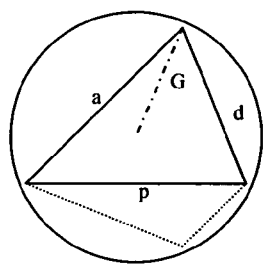
FIG. 11a provides a depiction of a first triangle used to characterize the radius of a digital image in accordance with an exemplary embodiment of the present invention.
Figure 11B:
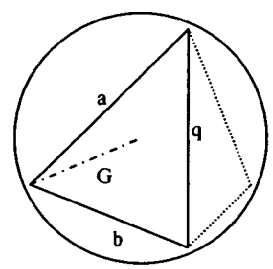
FIG. 11b provides a depiction of a second triangle used to characterize the radius of a digital image in accordance with an exemplary embodiment of the present invention.
Figure 11C:
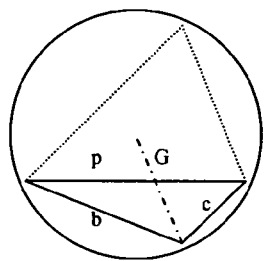
FIG. 11c provides a depiction of a third triangle used to characterize the radius of a digital image in accordance with an exemplary embodiment of the present invention.
Figure 11D:
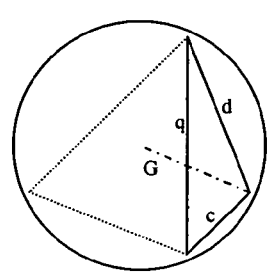
FIG. 11d provides a depiction of a fourth triangle used to characterize the radius of a digital image in accordance with an exemplary embodiment of the present invention.
Figure 11E:
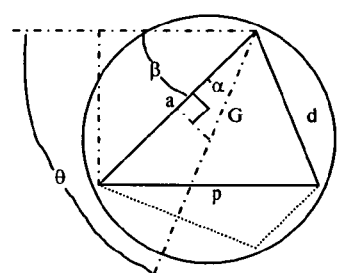
FIG. 11e provides a depiction of a first triangle used to characterize the center of a digital image in accordance with an exemplary embodiment of the present invention.
Figure 11F:
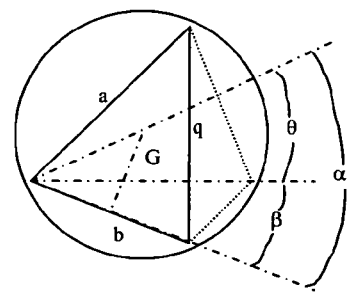
FIG. 11f provides a depiction of a second triangle used to characterize the center of a digital image in accordance with an exemplary embodiment of the present invention.
Figure 11G:
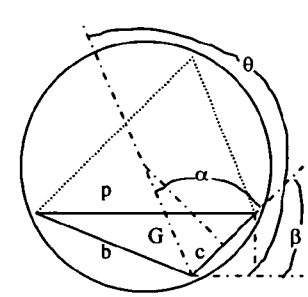
FIG. 11g provides a depiction of a third triangle used to characterize the center of a digital image in accordance with an exemplary embodiment of the present invention.
Figure 11H:
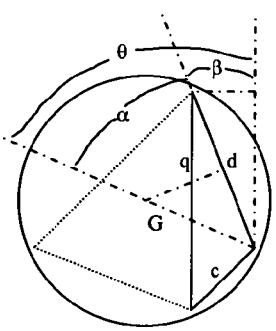
FIG. 11h provides a depiction of a fourth triangle used to characterize the center of a digital image in accordance with an exemplary embodiment of the present invention.

The quadrilateral generated by each set of five points is used to create four triangles. Each triangle is used to calculate the radius of a circle that would circumscribe the triangle. FIG. 11*a* provides a depiction of a first triangle used to characterize the radius of a digital image in accordance with an exemplary embodiment of the present invention. The variable "G" in FIG. 11*a* represents the radius of a circumscribed circle around a triangle described by sides "a," "d," and "p" as identified in FIG. 10. FIG. 11*b* provides a depiction of a second triangle used to characterize the radius of a digital image in accordance with an exemplary embodiment of the present invention. The variable "G" in FIG. 11b represents the radius of a circumscribed circle around a triangle described by sides "a," "b," and "q" as identified in FIG. 10. FIG. 11c provides a depiction of a third triangle used to characterize the radius of a digital image in accordance with an exemplary embodiment of the present invention. The variable "G" in FIG. 11c represents the radius of a circumscribed circle around a triangle described by sides "b," "c," and "q" as identified in FIG. 10. FIG. 11d provides a depiction of a fourth triangle used to characterize the radius of a digital image in accordance with an exemplary embodiment of the present invention. The variable "G" in FIG. 11d represents the radius of a circumscribed circle around a triangle described by sides "c," "d," and "q" as identified in FIG. 10. The radius is equal to the ratio of the products of the lengths of each side of the triangle to four times the triangle area. For example, the equation for the value of the radius in FIG. 11a is:

$$G = \frac{a \cdot d \cdot p}{4 \cdot (\text{area of } \Delta adp)}$$

Once the radius of the circumscribed circle about the four triangles is determined at step 910, then the circles' centers are determined, at step 920. To accomplish this determination, three angles are calculated based on the geometry of the four triangles depicted in FIGS. 11a through 11d, angles α, β and θ. The angle θ, the sum of angles α and β, represents the rotation angle of a vector having a known origin, magnitude, and starting direction. The origin of the vector is a convenient vertex on the describing triangle. The magnitude of the vector is the radius of the circumscribed circle. The starting direction of rotation for the vector is either a convenient horizontal or vertical reference off the origin. FIGS. 11e through 11h illustrate the location of the angles for the triangles in FIGS. 11a through 11d, respectively. Trigonometric functions are used to solve for angles α and β, in each case and the sum of the values for these two angles equals the value for angle θ.

Once angle θ is calculated, the expressions below are used to determine the center of the circle. Expression I represent the rotation matrixes for the AP x-ray images taken positive counter clockwise about an axis normal to the plane of the image. A similar expression would be developed for the lateral x-ray. In the expressions provided below, the axis normal to the plane of the x-ray is the "Z" axis. Expression J is the starting direction of a vector having a magnitude equal to the radius of the circumscribed circle for the AP x-ray image. Again, a similar expression would be developed for the lateral x-ray. Expression K is the origin for the vector J that is to be rotated through the angle θ to arrive at the circumscribed circle's center. Expressions I, J and K use the subscript 0, 1, 2, and 3 to relate to the four triangles illustrated in FIGS. 11e through 11h, respectively. Also, expression K uses points from the quadrilateral in FIG. 10, points $E_0$, $E_1$, $E_2$, $E_3$, $E_4$, and $E_5$. These six variables refer to the x coordinate of the central point, the y coordinate of the central point, the y coordinate of the top point, the x coordinate of the right point, the y coordinate of the bottom point, and the x coordinate of the left point, respectively, used to form the quadrilateral used to determine the radius and center of the circular image. $L_0$, $L_1$, $L_2$, and $L_3$ represent the centers of the four circles.

$$I_0 = \begin{bmatrix} \cos(\theta_0) & \sin(\theta_0) & 0 \\ -\sin(\theta_0) & \cos(\theta_0) & 0 \\ 0 & 0 & 1 \end{bmatrix}$$

$$I_1 = \begin{bmatrix} \cos(\theta_1) & \sin(\theta_1) & 0 \\ -\sin(\theta_1) & \cos(\theta_1) & 0 \\ 0 & 0 & 1 \end{bmatrix}$$

$$I_2 = \begin{bmatrix} \cos(\theta_2) & \sin(\theta_2) & 0 \\ -\sin(\theta_2) & \cos(\theta_2) & 0 \\ 0 & 0 & 1 \end{bmatrix}$$

$$I_3 = \begin{bmatrix} \cos(\theta_3) & \sin(\theta_3) & 0 \\ -\sin(\theta_3) & \cos(\theta_3) & 0 \\ 0 & 0 & 1 \end{bmatrix}$$

$$J_0 = \begin{bmatrix} 0 \\ G_0 \\ 0 \end{bmatrix}$$

$$J_1 = \begin{bmatrix} G_1 \\ 0 \\ 0 \end{bmatrix}$$

$$J_2 = \begin{bmatrix} 0 \\ -G_2 \\ 0 \end{bmatrix}$$

$$J_3 = \begin{bmatrix} -G_3 \\ 0 \\ 0 \end{bmatrix}$$

$$K_0 = \begin{bmatrix} E_1 \\ E_2 \\ 0 \end{bmatrix}$$

$$K_1 = \begin{bmatrix} E_5 \\ E_0 \\ 0 \end{bmatrix}$$

$$K_2 = \begin{bmatrix} E_1 \\ E_4 \\ 0 \end{bmatrix}$$

$$K_3 = \begin{bmatrix} E_3 \\ E_0 \\ 0 \end{bmatrix}$$

$$L_0 = I_0 \cdot J_0 + K_0$$
$$L_1 = I_1 \cdot J_1 + K_1$$
$$L_2 = I_2 \cdot J_2 + K_2$$
$$L_3 = I_3 \cdot J_3 + K_3$$

At step 930, the images are filtered. First, the mean and variance for the radius of each circular image is determined, based on the four calculated values for each triangle. Then, the mean values are compared to maximum and minimum values set for the analysis. Any image with a radius below a minimum or above a maximum value are not considered further. These maximum and minimum values are based on the expected size of the circular images to be formed by the imaging devices attached to the fixator.

At step 940, the images on the AP x-ray are then sorted by the x and y coordinates of the image circle centers, as calculated above (or, for the lateral x-ray, by the y and z coordinates). The coordinates of each circle center locations are compared to other circle center locations. Values for these locations that are within a certain tolerance level are determined to represent the same circle. In these cases, the data for these same circles are averaged together to get a mean center location for that circular image.

Figure 12:
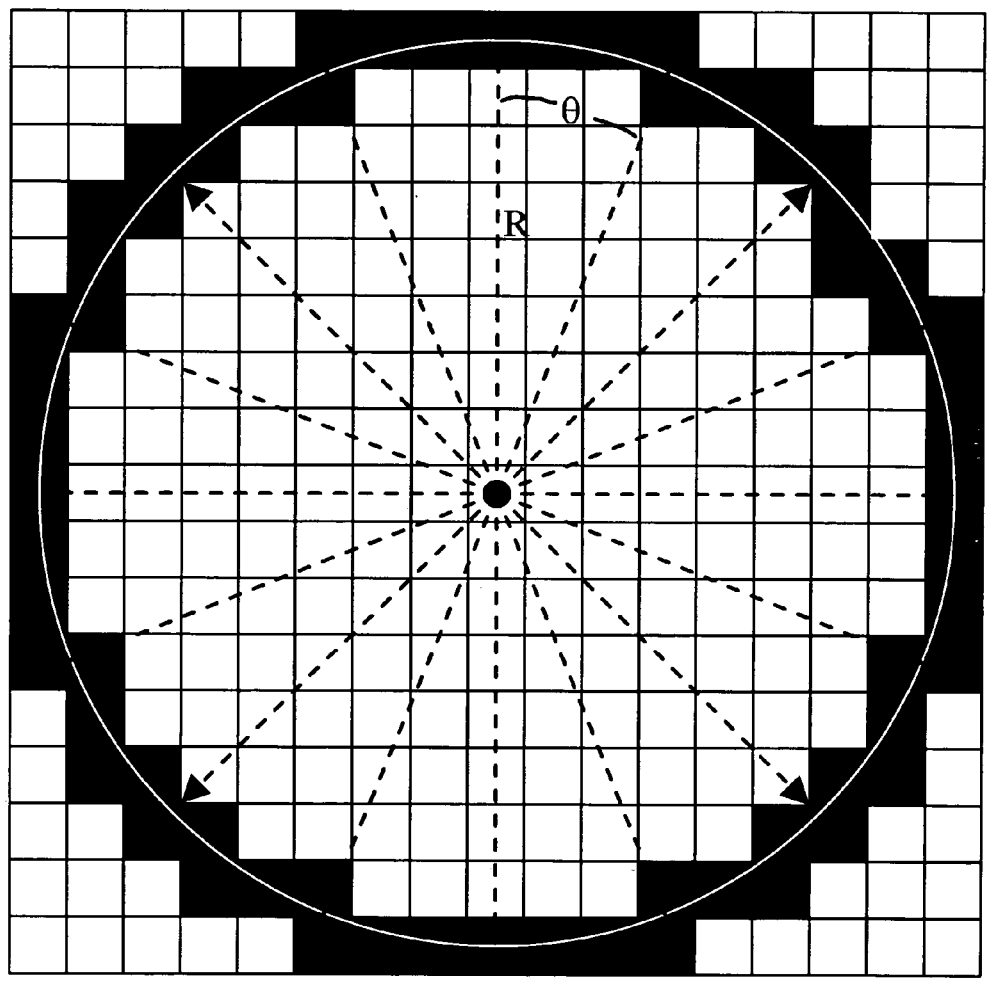
FIG. 12 provides a depiction of refining a circular image from a digital image using polar coordinates in accordance with an exemplary embodiment of the present invention.

At step 940, an additional refinement is performed. The possible circular images are evaluated using a polar coordinate system. The image is evaluated at a distance equal to the radius as calculated for the circular image from the center location. As the evaluation steps around a circle, for example in increments of 22.5 degrees, the image should have an intensity value of 255 at each point a distance equal to the radius away from the center. This refinement confirms that the image is a circle, and not, for example, a square, which might have passed earlier filters. FIG. 12 provides a depiction of refining a circular image from a digital image using polar coordinates in accordance with an exemplary embodiment of the present invention.

In an alternative embodiment, the possible circular images corresponding to balls on an imaging device may be identified by a user, such as by using a pointing device and a graphical user interface (GUI). A user could use the pointing device to click on a point inside a circle. This step could be used to speed computations, by manually filtering the images. This step could also be used If the quality of the x-ray prevents proper identification of the images associated with the imaging device.

Figure 13:
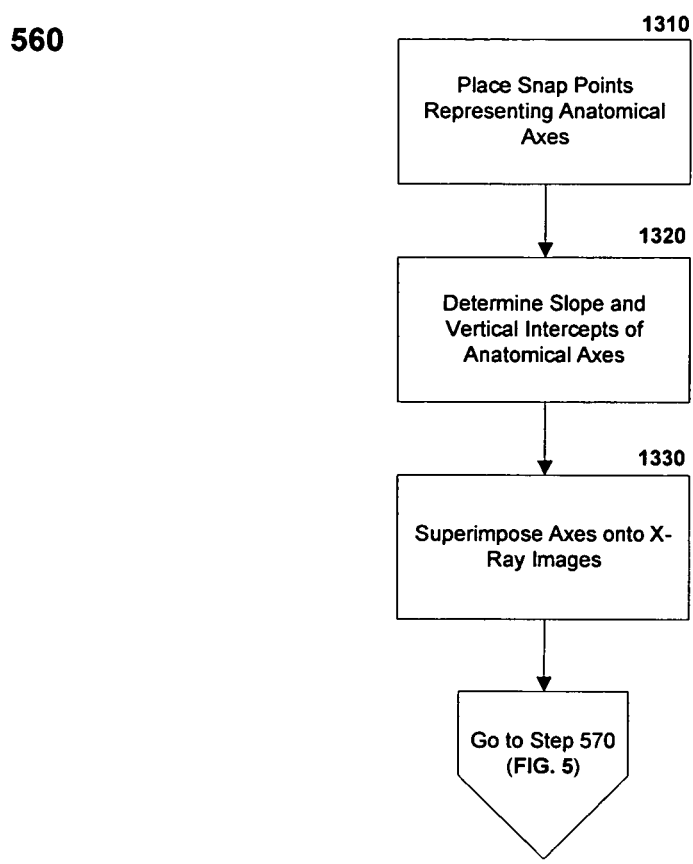
FIG. 13 provides a flow diagram for a process for determining bone fragment anatomical axes in accordance with an exemplary embodiment of the present invention.

FIG. 13 provides a flow diagram for a process 560 for determining bone fragment anatomical axes in accordance with an exemplary embodiment of the present invention. Referring to FIGS. 5 and 13, at step 1310, snap points are placed on images of the bone fragments. In this exemplary embodiment, snap points are placed on computer-generated images of the bone fragments based on the digital x-ray images, perhaps by using a GUI. One snap point is placed on each of the fractures such that, once in the reduced state, that is, once the deformity is corrected, these points are co-extensive. A second snap point is added along the anatomical axis of each fragment. From these points, the anatomical axes are developed.

Figure 14:
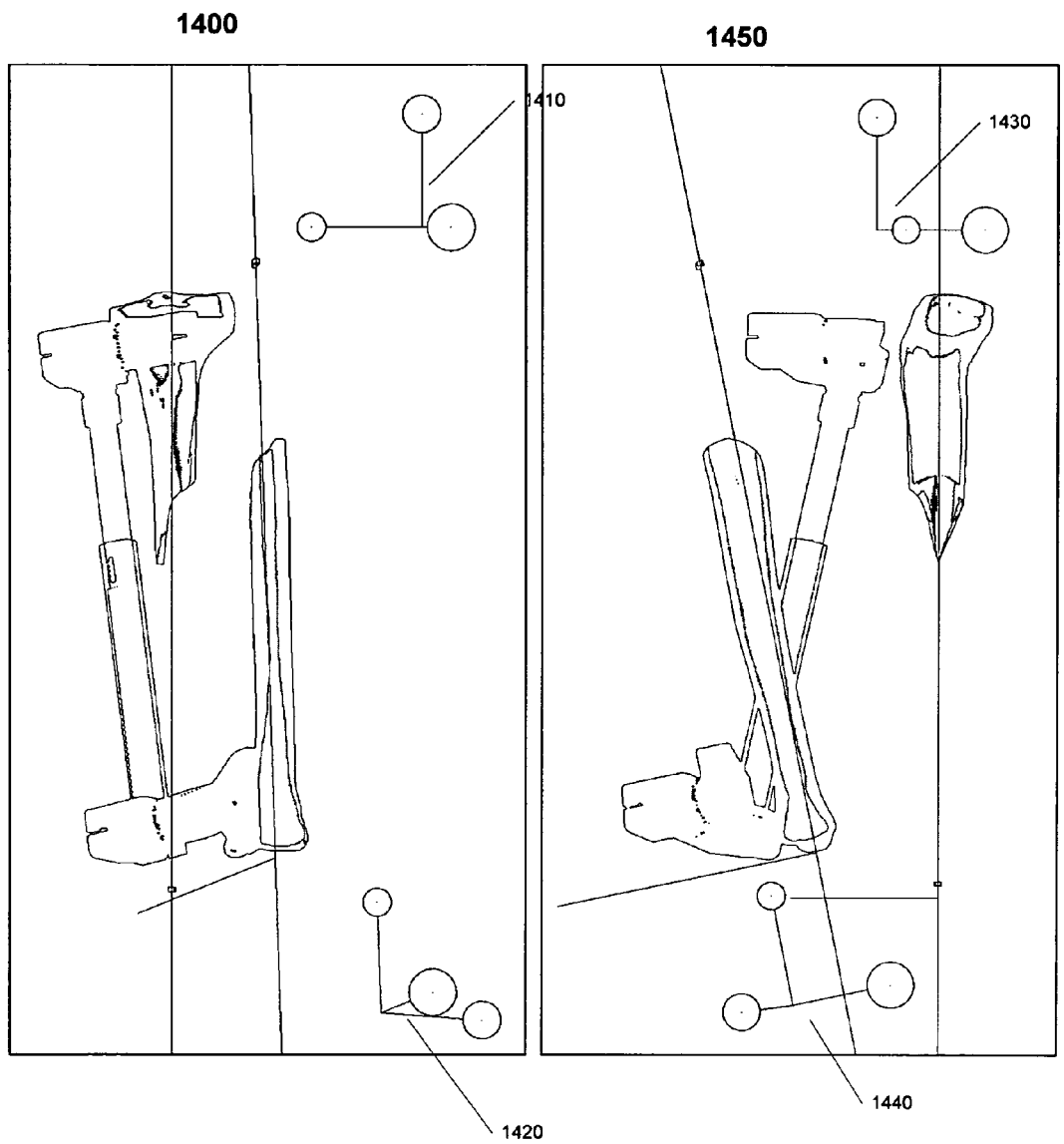
FIG. 14 provides a depiction of anatomical axes of bone fragments used to characterize the position of the fragments in accordance with an exemplary embodiment of the present invention.

At step 1320, the slope and vertical intercepts for the anatomical axes are determined. This determination is made using the basic line equation, y=mx+b, where "m" is the slope of the line and "b" is the vertical, or "y" intercept. At step 1330, an image of each line representing the anatomical axes are superimposed onto the x-ray images to confirm the analysis. The process 560 then moves to step 570 of process 210b. FIG. 14 provides a depiction of anatomical axis of bone fragments used to characterize the position of the fragments in accordance with an exemplary embodiment of the present invention. The image 1200 depicts the axes superimposed on an AP x-ray and the image 1250 shows the same image superimposed on a lateral x-ray. The features 1410, 1420, 1430, 1440 illustrate the orientation of the imaging devices relative to the fragments.

Figure 15:
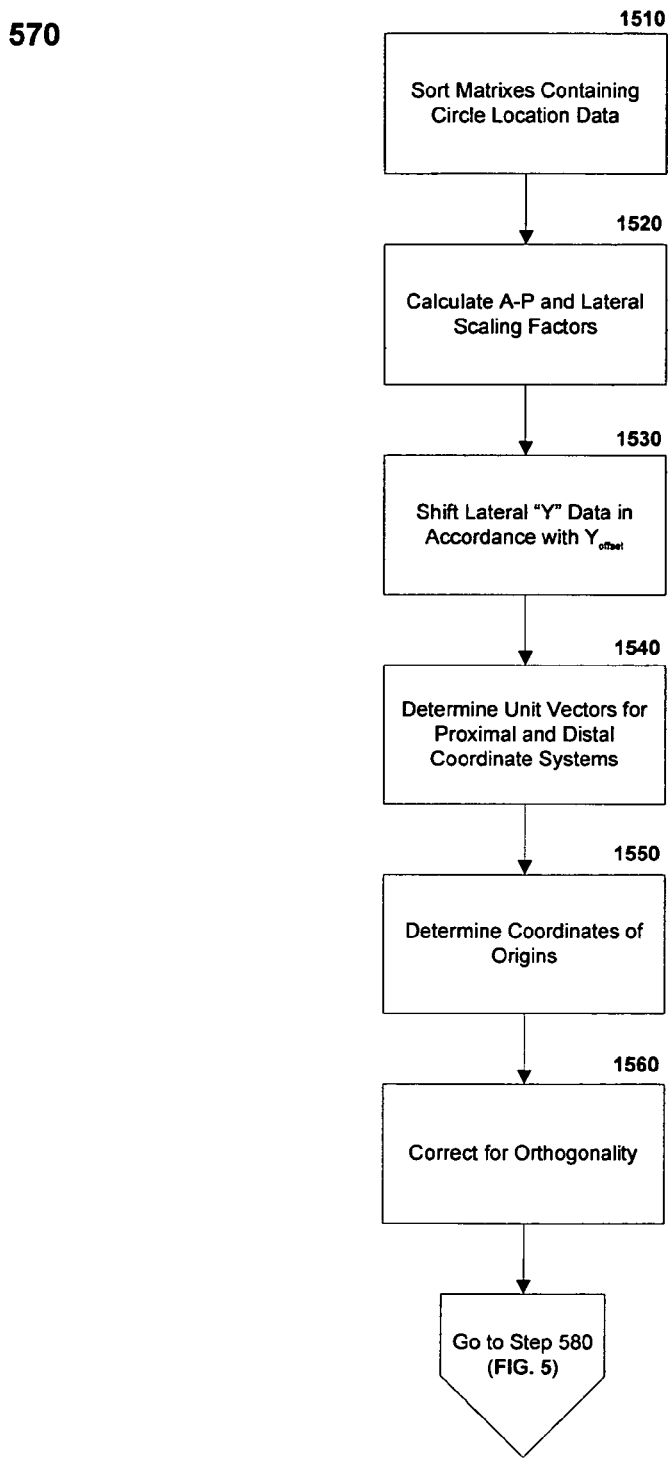
FIG. 15 provides a flow diagram for a process for characterizing proximal and distal coordinate systems in accordance with an exemplary embodiment of the present invention.

FIG. 15 provides a flow diagram for a process 570 for characterizing proximal and distal coordinate systems in accordance with an exemplary embodiment of the present invention. Referring to FIGS. 5 and 15, at step 1510, the final matrixes containing the circle location and radius data are sorted by center location. This sorting separates the circles representing the imaging device attached to the distal end of the fixator from the circles representing the imaging device attached to the proximal end of the fixator.

At step 1520, scaling factors are calculated for the two x-ray images. The physical orientation of the x-ray machine and medium, such as film, may cause the size of projected images to differ from the actual size of the structure that formed the image. The scaling factor is the ratio of the sum of the diameters of the six balls as measured by the process described above and the actual sum of the diameters of the six balls.

At step 540, the center and radius of the circular images on the x-rays as a result of the imaging device are determined. For the AP x-ray, the x and y coordinates of the ball centers were determined. From the lateral x-ray, the y and z coordinates were determined. Since two values for the y coordinate for each circle was determined, an offset for the lateral x-ray, as compared to the AP x-ray, can be determined. This determination is made at step 1530, with the offset value set to the average of the offsets for the six circle centers.

At step 1540, unit vectors for each of the balls on the imaging devices are determined. One endpoint of a unit vector is the circle center. The length of the vector is the length of the rod connecting the ball to the common point on the imaging device. At step 1550, a simultaneous solution of the equations representing the vectors allows for the origin, or common point, for each imaging device to be located on the digital image. In an alternative embodiment, a fourth ball could be located at the origin, and this step skipped.

At step 1560, the orthogonality of the system can be checked. Possible distortion of the x-ray image may cause the image from the imaging device to not be orthogonal. In this step, the orthogonality is check and the distortion noted. If the distortion level exceeds a threshold value, then the images may be corrected, using the orientation of the circular images of the imaging device to serve as the model for adjusting the image. The process 570 then moves to step 580 of process 210b.

FIG. 16 provides a depiction of an axis system for a device used to project images on a digital image in accordance with an exemplary embodiment of the present invention. This image 1600 illustrates the balls of varying size orthogonally opposed to one another and radiating from a common origin. One skilled in the art would appreciate that an orthogonal system does not need to be used. Instead, any coordinate system could be used, as long as the system is known, in other words, as long as the analyst knows the physical configuration of the imaging devices. For example, computational speed and accuracy may be enhanced by maximizing the distance between the balls, thus avoid clutter in the image. This maximum spacing may be facilitated by using a non-orthogonal coordinate system.

Figure 17:
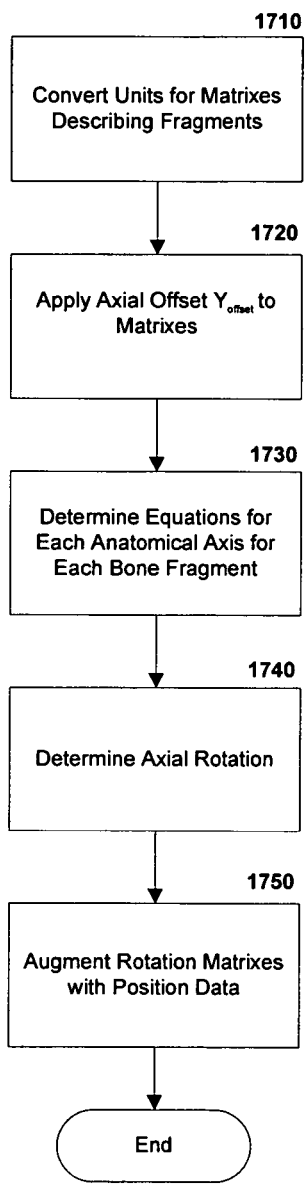
FIG. 17 provides a flow diagram for a process for characterizing bone fragments in accordance with an exemplary embodiment of the present invention.

FIG. 17 provides a flow diagram for a process 580 for characterizing bone fragments in accordance with an exemplary embodiment of the present invention. Referring to FIGS. 5, 15, and 17, at step 1710, using the scaling factors determined at step 1520, the description of the fractures, as represented by the anatomical axes determined at step 560, are converted from bitmap units to actual units. At step 1720, the axial offset, as calculated at step 1530, is applied to the matrixes describing the fragments.

At step 1730, the equations for each anatomical axis for each fragment is again calculated, based on the manipulated matrixes. To determine the equation of the anatomic axis for each of the bone fragments, proximal and distal, first, the equation of a plane that is normal to the AP x-ray image within which the proximal fragment anatomic axis lies is determined. Also determine is the equation of a plane that is normal to the AP x-ray image within which the distal fragment anatomic axis lies. The same process is repeated for the lateral x-ray. Then the intersection of the pair of planes corresponding to each fragment is taken and the equation of a line that is co-linear with the anatomic axis of the subject fragment is computed.

At step 1740, the axial rotation of the fragments is determined. Since the x-ray characterization algorithm cannot ascertain the axial rotation of the fragments an assumption could be made that both anterior anatomic markers, if present, the lines of which could be projected onto a plane normal to both the AP and lateral x-rays, would have the projected lines pointing in a directly anterior direction. An anatomical marker is a reference structure in the body associated with the bone fragment struction or other tissue structure. Anatomic markers would be, for instance, a foot for a distal fragment and a knee cap for a proximal fragment. Since this situation is not always the case, a clinical evaluation of one fragment's rotation relative to the other would generally be made, with the observation being made along the axis of one of the fragments with the anatomic marker of the other being projected onto a plane that would be normal to the anatomic axis of the reference fragment. This observed angulation would then be used to transform the coordinate system describing the other fragment, which initially would have a zero axial rotation value.

One skilled in the art would appreciate that the technique of process 210b, as described in FIG. 5, above, could be applied to other medical applications. For example, an imaging device could be projected onto an x-ray containing an internal organ system. Then, by evaluating the projected circles, a physician could characterize the imaged organ system. This imaging process could avoid the need for a more evasive procedure on the patient. The digital image would be evaluated in a method similar to that of FIG. 5. The projected balls would be located. Their orientation on the x-ray image would allow a characterization of how specific tissue is oriented, in a manner similar to characterizing bone fragments.

One skilled in the art would appreciate that the present invention supports a method for determining the proper configuration of a fixator or other medical device to correct a given deformity by solving the simultaneous equations representing the kinematic chain for the device. One skilled in the art would also appreciate that x-rays, clinical evaluations, or a combination of both may be used to determine the distal and proximal mounting characteristics, including the use of digital x-rays with images from an imaging device to reduce or eliminate the needs for a physician to take measurements. The technique can be expanded to other medical evaluations.

What is claimed is:

1. A method for determining a transform of a deformity-correcting fixator in a treatment plan to treat a bone condition, the method comprising the steps of:
    generating a first two-dimensional digital x-ray image comprising a first plurality of identifiable shapes associated with the deformity-correcting fixator;
    generating a second two-dimensional digital x-ray image comprising a second plurality of identifiable shapes associated with the deformity-correcting fixator, the second digital x-ray image taken at an angle relative to the first digital x-ray image;
    in a computer, characterizing a mounting condition for a first bone fragment attachment apparatus of the deformity correcting fixator and a second bone fragment attachment apparatus of the deformity correcting fixator based on the first and second images, wherein characterizing a mounting condition includes
        a) calculating a three-dimensional coordinate system to relate the deformity correcting fixator to the bone, comprising:
            i) automatically identifying outlines of the first and second pluralities of identifiable shapes and determining size of the identifiable shapes in the first and second two-dimensional digital x-ray images,
            ii) scaling the first and second two-dimensional digital x-ray images by comparing the determined size of the identifiable shapes in the first and second two-dimensional digital x-ray image to pre-stored size values corresponding to the actual size of the shapes of the identifiable shapes associated with the deformity-correcting fixator,
            iii) identifying a reference origin of the deformity correcting fixator in each of the first and second two-dimensional digital x-ray images based on the scaled identifiable shapes in order to relate the first plurality of identifiable shapes in the first two-dimensional digital x-ray image to the second plurality of identifiable shapes in the second two-dimensional digital x-ray image, and
            iv) generating the three-dimensional coordinate system based on the location of the reference origin and the location of two or more of the additional identifiable shapes,
        b) characterizing a transform of first and second bone fragments for comparison to the deformity correcting fixator comprising:
            i) receiving an input representing a first line extending along a first bone fragment in the first two-dimensional digital x-ray image,
            ii) generating an equation for a first plane perpendicular to the first line extending along the first bone fragment,
            iii) receiving an input representing a second line extending along the first bone fragment in the second two-dimensional digital x-ray image,
            iv) generating an equation for a second plane perpendicular to the second line extending along the first bone fragment,
            v) calculating an intersection of the first plane and the second plane to identify a line co-linear with a reference axis of the of the first bone fragment,
            vi) repeating steps i) to v) for the second bone fragment to identify a line co-linear with the reference axis of the second bone fragment,
        c) establishing a first transform between at least one of the first and second bone fragments and at least one of the first and second bone fragment attachment apparatuses of the deformity correction fixator, the first bone fragment attachment apparatus being fixed relative to the first bone fragment and the second bone fragment attachment apparatus being fixed relative to the second bone fragment in the three-dimensional coordinate system, and
    calculating a set of fixator settings corresponding to a desired second transform of the first bone fragment relative to the second bone fragment with the established first transform.

2. The method of claim 1, comprising reconfiguring the deformity correcting fixator based on the set of fixator settings.

3. The method of claim 1, comprising calculating a successive set of fixator settings corresponding to a desired third transform of the first bone fragment relative to the second bone fragment with the established first transform and with the desired second transform.

4. The method of claim 3, comprising reconfiguring the deformity correcting fixator based on the successive set of fixator settings.

5. The method of claim 3, wherein the deformity-correcting fixator comprises a unilateral fixator and the first and second bone fragment attachment apparatuses each comprise a first and a second compound movable joint, the unilateral fixator also comprising a strut assembly, wherein each compound movable joint provides deformity correction in two degrees of freedom, and wherein the strut assembly provides a third degree of freedom for each compound movable joint.

6. The method of claim 1, wherein the second two-dimensional digital x-ray image is taken at an oblique angle relative to the first two-dimensional digital x-ray image.

7. The method of claim 1, wherein the first and second pluralities of identifiable shapes are spherical shapes corresponding to an imaging device attached to the deformity correcting fixator.

8. The method of claim 1, wherein characterizing a transform of the first and second bone fragments comprises:
   determining an axial rotation for the first bone fragment attachment apparatus;
   determining an anterior-posterior rotation for the first bone fragment attachment apparatus;
   determining a lateral rotation for the first bone fragment attachment apparatus;
   determining a pin offset for the first bone fragment attachment apparatus; and
   determining the bone length.

9. The method of claim 1, wherein the step of calculating a three dimensional coordinate system to relate the deformity correcting fixator to the bone comprises:
   identifying a center for each identifiable shape of the first plurality of identifiable shapes;
   identifying unit vectors for each identifiable shape of the first plurality of identifiable shapes; and
   determining said reference origin by generating a solution to equations representing the identified unit vectors.

10. The method of claim 1, wherein the plurality of identifiable shapes corresponds to an imaging device comprising three balls, wherein the first ball is connected to a first end of a first rod, the second ball is connected to a first end of a second rod, the third ball is connected to a first end of a third rod, and second end of the first rod is connected to a second end of the second rod and a second end of the third rod.

11. The method of claim 10, wherein the first rod, the second rod, and the third rod are orthogonally opposed.

12. The method of claim 10, wherein the point where the second end of the first rod is connected to the second end of the second rod and the second end of the third rod comprises a fourth ball.

13. The method of claim 1, comprising using an anatomical marker as a reference structure to determine axial rotation of the second bone fragment relative to the first bone fragment, and using the determined axial rotation to transform the coordinate system describing the second bone fragment.

14. The method of claim 1, wherein the deformity correcting fixator comprises an imaging device, and wherein the identifiable shapes are associated with the imaging device.

15. The method of claim 1, wherein receiving an input comprises receiving an input from a GUI.

16. The method of claim 1, wherein characterizing a transform of first and second bone fragments further comprises clinically assessing the axial rotation of at least one of the first and second bone fragments relative to the other of the first and second bone fragments with regard to a global coordinate system.

17. The method of claim 1, further comprising:
   iteratively calculating successive sets of fixator settings using the first transform and prior sets of fixator settings to yield a set of fixator settings resulting in the desired transform aligning the first and second bone segments.

* * * * *

UNITED STATES PATENT AND TRADEMARK OFFICE
CERTIFICATE OF CORRECTION

| | | |
|---|---|---|
| PATENT NO. | : 8,419,732 B2 | Page 1 of 1 |
| APPLICATION NO. | : 10/714225 | |
| DATED | : April 16, 2013 | |
| INVENTOR(S) | : Michael W. Mullaney | |

It is certified that error appears in the above-identified patent and that said Letters Patent is hereby corrected as shown below:

In the Specifications:

Column 5, Line 62, delete the portion of text reading "(ryj_off y)" and replace with --(ryj_off_y)--.

Column 6, Line 2, delete the portion of text reading "(mdj_off_x)" and replace with --(mrj_off_x)--.

Column 13, Line 10, delete the portion of text reading "sides "b", "c", and "q" as" and replace with --sides "b", "c", and "p" as--.

Signed and Sealed this
Eleventh Day of June, 2013

Teresa Stanek Rea
*Acting Director of the United States Patent and Trademark Office*